US007576262B2

(12) United States Patent
Wang et al.

(10) Patent No.: US 7,576,262 B2
(45) Date of Patent: Aug. 18, 2009

(54) MODIFIED GENE-SILENCING RNA AND USES THEREOF

(75) Inventors: Ming-Bo Wang, Kaleen (AU); Peter Waterhouse, Canberra (AU)

(73) Assignee: Commonwealth Scientific and Industrial Research Organization, Campbell (AU)

( * ) Notice: Subject to any disclaimer, the term of this patent is extended or adjusted under 35 U.S.C. 154(b) by 860 days.

(21) Appl. No.: 10/385,521

(22) Filed: Mar. 12, 2003

(65) Prior Publication Data

US 2003/0180945 A1 Sep. 25, 2003

Related U.S. Application Data

(60) Provisional application No. 60/363,851, filed on Mar. 14, 2002.

(51) Int. Cl.
*C12N 15/82* (2006.01)
*C12N 5/10* (2006.01)
*A01H 5/00* (2006.01)

(52) U.S. Cl. .................... 800/286; 435/419; 435/468; 435/320.1

(58) Field of Classification Search .................... None
See application file for complete search history.

(56) References Cited

U.S. PATENT DOCUMENTS

| 4,873,191 A | 10/1989 | Wagner et al. |
| 5,037,745 A | 8/1991 | McAllister |
| 5,190,931 A | 3/1993 | Inouye |
| 5,908,779 A | 6/1999 | Carmichael et al. |

FOREIGN PATENT DOCUMENTS

| EP | 0 223 399 A1 | 5/1987 |
| EP | 0 240 208 A2 | 10/1987 |
| EP | 0 467 349 A1 | 1/1992 |
| WO | WO 89/03887 | 5/1989 |
| WO | WO 89/10396 | 11/1989 |
| WO | WO 92/13956 | 8/1992 |
| WO | WO 95/15394 | 6/1995 |
| WO | WO 96/06932 | 3/1996 |
| WO | WO 97/13865 | 4/1997 |
| WO | WO 98/05770 | 2/1998 |
| WO | WO 01/12824 A1 | 2/2001 |
| WO | WO 02/00894 A2 | 1/2002 |
| WO | WO 02/00904 A2 | 1/2002 |
| WO | WO 02/10365 A2 | 2/2002 |

OTHER PUBLICATIONS

Thomas et al., Plant Journal, 2001, vol. 25, pp. 417-425.*
J.M. Alonso et al., "EIN2, a Bifunctional Transducer of Ethylene and Stress Responses in *Arabidopsis*", *Science*, Jun. 25, 1999, vol. 284, p. 2148-2152, American Association for the Advancement of Science with the assistance of Stanford University Libraries' HighWire Press, Stanford, California, USA.
Yong-Qiang An et al, "Conserved Expression of the *Arabidopsis ACT1* and *ACT3* Actin Subclass in Organ Primordia and Mature Pollen", *The Plant Cell*, vol. 8, p. 15-30, Jan. 1996, American Society of Plant Physiologists, Rockville, Maryland USA.
F. Bussiere et al., "Compilation and Analysis of Viroid and Viroid-Like RNA Sequences", *Nucleic Acids Research*, 1996, vol. 24, No. 10, p. 1793-1798, Oxford University Press, Oxford, United Kingdom.
E. Butler et al, "Bacteriophage SP6-specific RNA Polymerase", *The Journal of Biological Chemistry*, vol. 257, No. 10, Issue of May 25, p. 5772-5778, American Society for Biochemistry and Molecular Biology, Bethesda, MD, USA.
R.R.D. Croy, Plant Molecular Biology Labfax: 1993, Blackwell Scientific Publications, UK, p. 180-182.
M. Dalrymple et al., "Genetically Modified Livestock for the Production of Human Proteins in Milk", *Biotechnol. Genet. Eng. Rev.*, vol. 15, p. 33-49, Apr. 1998, Intercept, Newcastle upon Tyne, UK.
B. Davis et al, "Expansion of CUG Trinucleotide Repeat in the 3' Untranslated Region of Myotonic Dystrophy Protein Kinase Transcripts Results in Nuclear Retention of Transcripts", *Proc. Natl. Acad. Sci. USA*, vol. 94, p. 7388-7393, National Academy of Sciences, USA.
J. Dunn et al., "Complete Nucleotide Sequence of Bacteriophase T7 DNA and the Locations of T7 Genetic Elements", *J. Mol. Biol.*, 1983, vol. 166, p. 477-535, Academic Press Inc., San Diego, CA USA.
J. Dunn et al, "Different Template Specificities of Phase T3 and T7 RNA Polymerases", *Nature New Biology*, vol. 230, Mar. 17, 1971, MacMillan Journals Limited, London England, p. 94-96.
C. Fagoaga et al, "A Citrus Exocortis Viroid Variant from Broad Bean (*Vicia faba* L.): Infectivity and Pathogenesis", *Journal of General Virology*, 1995, vol. 76, p. 2271-2277, Society for General Microbiology, London, UK.
A. Gleave, "A Versatile Binary Vector System with a T-DNA Organisational Structure Conductive to Efficient Integration of Cloned DNA Into the Plant Genome", *Plant Molecular Biology*, vol. 20, p. 1203-1207, 1992, Kluwer Academic Publisher,Dordrecht, The Netherlands.
M. Harpster et al, "Relative Strengths of the 35S Califlower Mosaic Virus, 1', 2', and Nopaline Synthase Promoters in Transformed Tobacco Sugarbeet and Oilseed Rape Callus Tissue", *Mol Gen Genet*, 1988, vol. 212, p. 181-190, Springer Verlag, Berlin, Germany.
J. Haseloff et al, "Viroid RNAs of Cadang-Cadang Disease of Coconuts", *Nature* vol. 299, p. 316-321, Nature Publishing Group, Hampshire, UK, 1982.
R. Hausmann, "Bacteriophase T7 Genetics" (book), *Current Topics in Microb, and Imm.*, 1976, p. 77-109, Berlin Springer Verlag, New York.
T. Herold et al, "Sequence Analysis of Five New Field Isolates Demonstrates that the Chain Length of Potato Spindle Tuber Viroid (PSTVd) is Not Strictly Conserved But as Variable as in Other Viroids", *Plant Molecular Biology*, vol. 19, p. 329-333, 1992,Kluwer Academic Publishers, Dordrecht, The Netherlands.

(Continued)

*Primary Examiner*—Ashwin Mehta
(74) *Attorney, Agent, or Firm*—Buchanan Ingersoll & Rooney, PC

(57) ABSTRACT

Methods and means for efficiently downregulating the expression of any gene of interest in eukaryotic cells and organisms are provided. To this end, the invention provides modified antisense and sense RNA molecules, chimeric genes encoding such modified antisense or sense RNA molecules and eukaryotic organisms such as plants, animals or fungi, yeast or molds, comprising the modified antisense and/or sense RNA molecules or the encoding chimeric genes.

35 Claims, 5 Drawing Sheets

OTHER PUBLICATIONS

Yau-Heiu Hsu et al, "Nucleotide Sequence of a Hop Stunt Viroid Variant Isolated from Citrus Growing in Taiwan", *Virus Genes*, 1994, vol. 9, No. 2, p. 193-195, Kluwer Academic Publishers, Boston, Manufactured in The Netherlands.

R. Hudspeth et al, "Structure and Expression of the Maize Gene Encoding the Phosphoenolpyruvate Caboxylase Isozyme Involved in C4 Photosynthesis", *Plant Molecular Biology*, 1989, vol. 12, p. 579-589, Kluwer Academic Publishers, Dordrecht, The Netherlands.

M. Keil et al, "Both Wound-Inducible and Tuber-Specific Expression are Mediated by the Promoter of a Single Member of the Potato Proteinase Inhibitor II Gene Family", *The EMBO Journal*, 1989, vol. 8, No. 5, p. 1323-1330, Oxford University Press, Oxford UK.

B. Keller et al, "Glycine-Rich Cell Wall Proteins in Bean: Gene Structure and Association of the Protein with the Vascular System", *The EMBO Journal*, vol. 7, No. 12, p. 3625-2633, 1988, IRL Press Limited, Oxford, England.

B. Keller et al, "Specific Expression of a Novel Cell Wall Hydroxyproline-Rich Glycoprotein Gene in Lateral Root Initiation", *Genes & Development* vol. 3, p. 1639-1646, 1989, Cold Spring Harbor Laboratory Press, Cold Spring Harbor, NY USA.

J. Klement et al., "Discrimination Between Bacteriophage T3 and T7 Promoters by the T3 and T7 RNA Polymerases Depends Primarily Upon a Three Base-pair Region Located 10 to 12 Base-pairs Upstream from the Start Site", *J. Mol. Biol.*, 1990, vol. 215, p. 21-29, Academic Press Limited, San Diego, CA, USA.

K. Koch et al, "Giant Hairpins Formed by CUG Repeats in Myotonic Dystrophy Messenger RNAs Might Sterically Block RNA Export Through Nuclear Pores", *J. Theor. Biol.*, 1998, vol. 192, p. 505-514, Academic Press, San Diego, CA USA.

K. Korsten et al, "The Strategy of Infection as a Criterion for Phylogenetic Relationships of Non-Coli Phages Morphologically Similar to Phage T7", *J. Gen. Virol*, 1979, vol. 43, p. 57-73, Society for General Microbiology, London, UK.

Lee et al, "Nucleotide Sequence of the Korean Strain of Hop Stunt Viroid (HSV)", *Nucleic Acids Research*, vol. 16, No. 17, 1988, IRL Press Limited, Oxford, England, p. 8708.

N.J. McGraw et al, "Sequence and Analysis of the Gene for Bacteriophage T3 RNA Polymerase", *Nucleic Acids Research*, vol. 13, No. 18, 1985, IRL Press Limited, Oxford, England, p. 6753-6766.

J. Peleman et al, "Structure and Expression Analyses of the S-Adenosylmethionine synthetase Gene Family in *Arabidopsis thaliana*", *Gene*, vol. 84, 1989, p. 359-369, Elsevier Science Publishers B.V., Oxford, UK.

M. Perry et al., "Transgenesis in Chickens", *Transgenic Research*, vol. 2, 1993, p. 125-133, Kluwer Academic Publishers, Dordrecht, The Netherlands.

N. Rudolph et al, "Biopharmaceutical Production in Transgenic Livestock", *TIBTECH*, 1999, vol. 17, p. 367-374, Elsevier Science Ltd. , Netherlands.

B. Tian et al, "Expanded CUG Repeat RNAs Form Hairpins That Activate the Double-Stranded RNA-Dependent Protein Kinase PKR", *RNA*, 2000, vol. 6, p. 79-87, Cambridge University Press, Printed in the USA.

H. Towle, "Purification and Characterization of Bacteriophage gh-1-induced Deoxyribonucleic Acid-dependent Ribonucleic Acid Polymerase from *Pseudomonas putida*", *The Journal of Biological Chemistry*, vol. 250, No. 5, Issue of Mar. 10, 1975, pp. 1723-1733, American Society for Biochemistry and Molecular Biology, Bethesda, MD, USA.

J. Visvader et al, "Eleven New Sequence Variants of Citrus Exocortis viroid and the Correlation of Sequence With Pathogenicity", *Nucleic Acids Research*, vol. 13, No. 8, 1985, IRL Press Limited, Oxford, England, p. 2907-2920.

M. Wang et al, "Improved Vectors for *Agrobacterium Tumefaciens*-Mediated Transformation of Monocot Plants", *Acta Horticulturae*, vol. 461, p. 401-407, The International Society for Horticultural Science, Leuven, Belgium, 1998.

S. Wesley et al, "Construct Design for Efficient, Effective and High-Throughput Gene Silencing in Plants", *The Plant Journal*, 2001, vol. 27, No. 6, p. 581-590, Blackwell Science Ltd., Oxford, UK.

I. Wilmut et al, "Viable Offspring Derived From Fetal and Adult mammalian Cells", *Nature*, vol. 385, Feb. 27, 1997, Nature Publishing Group, Hampshire, UK.

I. Wilmut et al, "Embryonic and Somatic Cell Cloning", *Reprod. Fertil. Dev.*, 1998, vol. 10, p. 639-643.

Y. Zhao et al, "Use of a Vector Based on *Potato virus X* in a Whole Plant Assay to Demonstrate Nuclear Targeting of *Potato Spindle Tuber Viroid*", *Journal of General Virology*, 2001, vol. 82, p. 1491-1497, Society for General Microbiology, London, UK.

M. Zuker, "On Finding All Suboptimal Foldings of an RNA Molecule", *Science*, 1989, vol. 244, p. 48-52, American Association for the Advancement of Science with the assistance of Stanford University Libraries' HighWire Press, Stanford, California, USA.

Asuka Itaya et al., "Potato Spindle Tuber Viroid as Inducer of RNA Silencing in Infected Tomato", *MPMI*, (2001) vol. 14, No. 11, pp. 1332-1334, The American Phytopathological Society, St. Paul, Minnesota, USA.

Ioannis Papefthimiou et al, "Replicating Potato Spindle Tuber Viroid RNA is Accompanied by Short RNA Fragments that are Characteristic of Post-Transcriptional Gene Silencing", *Nucleic Acids Research*, (2001) vol. 29, No. 11, pp. 2395-2400, Oxford University Press, Oxford, England.

Di Serio et al., "Sense- and antisense-mediated gene silencing in tobacco is inhibited by the same viral suppressors and is associated with accumulation of small RNAs," *PNAS*, 2001, vol. 98, No. 11, pp. 6506-6510, National Academy of Sciences, Washington, D.C.

Smith et al., "Total silencing by intronspliced hairpin RNAs," *Nature*, 2000, vol. 407, pp. 319-320.

Colman, "Production of therapeutic proteins in the milk of transgenic livestock," *Biochem. Soc. Symp.*, 1998, vol. 63, pp. 141-147, London Portland Press, London UK.

* cited by examiner

A

B

C

D

E

F

A.

B.

A.

B.

SEQUENCE LISTING

<160> NUMBER OF SEQ ID NOS: 15

<210> SEQ ID NO 1
<211> LENGTH: 29
<212> TYPE: DNA
<213> ORGANISM: Artificial
<220> FEATURE:
<223> OTHER INFORMATION: oligonucleotide primer for the PCR
      amplification of the genome of PSTVd RG1

<400> SEQUENCE: 1
cgcagatctc ggaactaaac tcgtggttc                                    29

<210> SEQ ID NO 2
<211> LENGTH: 27
<212> TYPE: DNA
<213> ORGANISM: Artificial
<220> FEATURE:
<223> OTHER INFORMATION: oligonucleotide primer for the PCR
      amplification of the genome of PSTVd RG1

-continued

<400> SEQUENCE: 2
gcgagatcta ggaaccaact gcggttc 27

<210> SEQ ID NO 3
<211> LENGTH: 359
<212> TYPE: DNA
<213> ORGANISM: Potato spindle tuber viroid

<400> SEQUENCE: 3
cggaactaaa ctcgtggttc ctgtggttca cacctgacct cctgacaaga aaagaaaaaa 60
gaaggcggct cggaggagcg cttcagggat ccccggggaa acctggagcg aactggcaaa 120
aaaggacggt ggggagtgcc cagcggccga caggagtaat tcccgccgaa acagggtttt 180
cacccttcct ttcttcgggt gtccttcctc gcgcccgcag gaccacccct cgcccccttt 240
gcgctgtcgc ttcggctact acccggtgga aacaactgaa gctcccgaga accgcttttt 300
ctctatctta cttgctccgg ggcgagggtg tttagccctt ggaaccgcag ttggttcct 359

<210> SEQ ID NO 4
<211> LENGTH: 369
<212> TYPE: DNA
<213> ORGANISM: Australian grapevine viroid

<400> SEQUENCE: 4
tgggcaccaa ctagaggttc ctgtggtact caccgaaggc cgcgaacgta ggaaagaaaa 60
agatagaaaa gctgggtaag actcacctgg cgactcgtcg tcgacgaagg gtcctcagca 120
gagcaccggc aggaggcgct atgcaggaac gctaggggtc ctccagcgga ggactgaaga 180
aactccggtt tcttctttca ctctgtagct ggaatccctg ttgcgcttgc tggcgaaacc 240
tgcagggaag ctagctgggt cccgctagtc gagcggactc gtcccagcgg tcccaaccag 300
ttttctttat cctatttttc ctgcgggcgc ccggtcgtgg ttaccctgga gctccctgtt 360
tggaggccc 369

<210> SEQ ID NO 5
<211> LENGTH: 254
<212> TYPE: DNA
<213> ORGANISM: Coconut tinangaja viroid

<400> SEQUENCE: 5
ctggggaatt cccacggctc ggcaaaataa aagcacaaga gcgactgcta gagggatccc 60
cggggaaacc cctagcaacc gaggtaggga gcgtacctgg tgtcgccgat tcgtgctggt 120
tgggcttcgt cccttccgag cttcgatccg acgcccggcc gcttcctcgc cgaagctgct 180
acggagacta cccggtggat acaactcttt gcagcgccct gtgtaataaa agctcgagtc 240
cggtttgcgc ccct 254

<210> SEQ ID NO 6
<211> LENGTH: 360
<212> TYPE: DNA
<213> ORGANISM: Tomato planta macho viroid

<400> SEQUENCE: 6
cgggatcttt tccttgtggt tcctgtggta cacacctgac ctcctgacca gaaaagaaaa 60
aagaattgcg gccaaaggag cgcttcaggg atccccgggg aaacctggag cgaactggcg 120
aaggagtcgc ggctggggag tctcccagac aggagtaatc cccgctgaaa cagggttttc 180
acccttcctt tcttcgggtt tccttcctct gcggtcgaca ccctcgcccg cttctcttgc 240

```
gctgtcgctt cggagactac ccggtggaaa caactgaagc tcccaagcgc cgcttttttct    300 ctatcttgct ggctccgggg cgagggtgga aaaccctgga acccttcgaa aagggtccct    360
```

<210> SEQ ID NO 7
<211> LENGTH: 256
<212> TYPE: DNA
<213> ORGANISM: Hop latent viroid

<400> SEQUENCE: 7

```
ctggggaata cactacgtga cttacctgta tgatggcaag ggttcgaaga gggatccccg     60
gggaaaccta ctcgagcgag gcggagatcg agcgccagtt cgtgcgcggc gacctgaagt    120
tgcttcggct tcttcttgtt cgcgtcctgc gtggaacggc tccttctcca caccagccgg    180
agttggaaac tacccggtgg atacaactct tgagcgccga gctttacctg cagaagttca    240
cataaaaagt gcccat                                                    256
```

<210> SEQ ID NO 8
<211> LENGTH: 360
<212> TYPE: DNA
<213> ORGANISM: Tomato apical stunt viroid

<400> SEQUENCE: 8

```
cgggatcttt cgtgaggttc ctgtggtgct cacctgaccc tgcaggcatc aagaaaaaag     60
ataggagcgg gaaggaagaa gtccttcagg gatccccggg gaaacctgga ggaagtcgag    120 gtcggggggct tcggatcatt cctggttgag acaggagtaa tcccagctga acagggtttt   180
tcacccttcc tttcttctgg tttccttcct ctcgccggaa ggtcttcggc cctcgcccgg    240
agcttctctc tggagactac ccggtggaaa caactgaagc ttccacttcc acgctctttt    300
tctctatctt tgttgctctc cgggcgaggg tgaaagcccg tggaaccctg aatggtccct    360
```

<210> SEQ ID NO 9
<211> LENGTH: 786
<212> TYPE: DNA
<213> ORGANISM: Artificial
<220> FEATURE:
<223> OTHER INFORMATION: nucleotide sequence of the pdk2 intron

<400> SEQUENCE: 9

```
aagcttggta aggaaataat tattttcttt ttccttttta gtataaaata gttaagtgat     60
gttaattagt atgattataa taatatagtt gttataattg tgaaaaaata atttataaat    120
atattgttta cataaacaac atagtaatgt aaaaaaatat gacaagtgat gtgtaagacg    180
aagaagataa aagttgagag taagtatatt attttttaatg aatttgatcg aacatgtaag    240
atgatatact agcattaata tttgttttaa tcataatagt aattctagct ggtttgatga    300
attaaatatc aatgataaaa tactatagta aaaataagaa taaataaatt aaaataaat    360 ttttttatga ttaatagttt attatataat taaatatcta taccattact aaatatttta    420
gtttaaaagt taataaatat tttgttagaa attccaatct gcttgtaatt tatcaataaa    480
caaaatatta ataacaagc taaagtaaca ataatatca aactaataga aacagtaatc      540
taatgtaaca aaacataatc taatgctaat ataacaaagc gcaagatcta tcattttata    600
tagtattatt ttcaatcaac attcttatta atttctaaat aatacttgta gttttattaa    660
cttctaaatg gattgactat taattaaatg aattagtcga acatgaataa acaaggtaac    720
atgatagatc atgtcattgt gttatcattg atcttacatt tggattgatt acagttggga    780
``` aagctt                                                                    786

<210> SEQ ID NO 10
<211> LENGTH: 4746
<212> TYPE: DNA
<213> ORGANISM: Arabidopsis thaliana

<400> SEQUENCE: 10
cttttctctc tctatctcta tctctcgtag cttgataaga gtttctctct tttgaagatc    60
cgtttctctc tctctcactg agactattgt tgttaggtca acttgcgatc atggcgattt   120
cgaaggtctg aagctgattt cgaatggttt ggagatatcc gtagtggtta agcatatgga   180
agtctatgtt ctgctcttgg ttgctctgtt agggcttcct ccatttggac caacttagct   240
gaatgttgta tgatctctct ccttgaagca gcaaataaga agaaggtctg gtccttaact   300
taacatctgg ttactagagg aaacttcagc tattattagg taaagaaaga ctgtacagag   360
ttgtataaca agtaagcgtt agagtggctt tgtttgcctc ggtgatagaa gaaccgactg   420
attcgttgtt gtgtgttagc tttggaggga atcagatttc gcgagggaag gtgttttaga   480
tcaaatctgt gaattttact caactgaggc ttttagtgaa ccacgactgt agagttgacc   540
ttgaatccta ctctgagtaa ttatattatc agatagattt aggatggaag ctgaaattgt   600
gaatgtgaga cctcagctag ggtttatcca gagaatggtt cctgctctac ttcctgtcct   660
tttggtttct gtcggatata ttgatcccgg gaaatgggtt gcaaatatcg aaggaggtgc   720
tcgtttcggg tatgacttgg tggcaattac tctgcttttc aattttgccg ccatcttatg   780
ccaatatgtt gcagctcgca taagcgttgt gactggtaaa cacttggctc agatctgcaa   840
tgaagaatat gacaagtgga cgtgcatgtt cttgggcatt caggcggagt tctcagcaat   900
tctgctcgac cttaccatgg ttgtgggagt tgcgcatgca cttaaccttt tgtttggggt   960
ggagttatcc actggagtgt ttttggccgc catggatgcg ttttttattc ctgttttcgc  1020
ctctttcctt gaaaatggta tggcaaatac agtatccatt tactctgcag gcctggtatt  1080
acttctctat gtatctggcg tcttgctgag tcagtctgag atcccactct ctatgaatgg  1140
agtgttaact cggttaaatg gagagagcgc attcgcactg atgggtcttc ttggcgcaag  1200
catcgtccct cacaattttt atatccattc ttattttgct ggggaaagta catcttcgtc  1260
tgatgtcgac aagagcagct tgtgtcaaga ccatttgttc gccatctttg gtgtcttcag  1320
cggactgtca cttgtaaatt atgtattgat gaatgcagca gctaatgtgt tcacagtac   1380
tggccttgtg gtactgactt tcacgatgc cttgtcacta atggagcagg tatttatgag  1440
tccgctcatt ccagtggtct ttttgatgct cttgttcttc tctagtcaaa ttaccgcact  1500
agcttgggct ttcggtggag aggtcgtcct gcatgacttc ctgaagatag aaatacccgc  1560
ttggcttcat cgtgctacaa tcagaattct tgcagttgct cctgcgcttt attgtgtatg  1620
gacatctggt gcagacggaa tataccagtt acttatattc acccaggtct ggtggcaat   1680
gatgcttcct tgctcggtaa taccgctttt ccgcattgct tcgtcgagac aaatcatggg  1740
tgtccataaa atccctcagg ttggcgagtt cctcgcactt acaacgtttt tgggatttct  1800
ggggttgaat gttgttttg ttgttgagat ggtatttggg agcagtgact gggctggtgg  1860
tttgagatgg aataccgtga tgggcacctc gattcagtac accactctgc ttgtatcgtc  1920
atgtgcatcc ttatgcctga tactctggct ggcagccacg ccgctgaaat ctgcgagtaa  1980
cagagcggaa gctcaaatat ggaacatgga tgctcaaaat gctttatctt atccatctgt  2040
tcaagaagag gaaattgaaa gaacagaaac aaggaggaac gaagacgaat caatagtgcg  2100

```
gttggaaagc agggtaaagg atcagttgga tactacgtct gttactagct cggtctatga    2160
tttgccagag aacattctaa tgacggatca agaaatccgt tcgagccctc cagaggaaag    2220
agagttggat gtaaagtact ctacctctca agttagtagt cttaaggaag actctgatgt    2280
aaaggaacag tctgtattgc agtcaacagt ggttaatgag gtcagtgata aggatctgat    2340
tgttgaaaca aagatggcga aaattgaacc aatgagtcct gtggagaaga ttgttagcat    2400
ggagaataac agcaagttta ttgaaaagga tgttgaaggg gtttcatggg aaacagaaga    2460
agctaccaaa gctgctccta caagcaactt tactgtcgga tctgatggtc ctccttcatt    2520
ccgcagctta agtggggaag ggggaagtgg gactggaagc cttccacggt tgcaaggttt    2580
gggacgtgct gcccggagac acttatctgc gatccttgat gaattttggg acatttata    2640
tgattttcat gggcaattgg ttgctgaagc cagggcaaag aaactagatc agctgtttgg    2700
cactgatcaa aagtcagcct cttctatgaa agcagattcg tttggaaaag acattagcag    2760
tggatattgc atgtcaccaa ctgcgaaggg aatggattca cagatgactt caagtttata    2820
tgattcactg aagcagcaga ggacaccggg aagtatcgat tcgttgtatg gattacaaag    2880
aggttcgtca ccgtcaccgt tggtcaaccg tatgcagatg ttgggtgcat atggtaacac    2940
cactaataat aataatgctt acgaattgag tgagagaaga tactctagcc tgcgtgctcc    3000
atcatcttca gagggttggg aacaccaaca accagctaca gttcacggat accagatgaa    3060
gtcatatgta gacaatttgg caaaagaaag gcttgaagcc ttacaatccc gtggagagat    3120
cccgacatcg agatctatgg cgcttggtac attgagctat acacagcaac ttgctttagc    3180
cttgaaacag aagtcccaga atggtctaac ccctggacca gctcctgggt ttgagaattt    3240
tgctgggtct agaagcatat cgcgacaatc tgaaagatct tattacgtg ttccatcttc    3300
tggcaatact gatactgttg gcgcagcagt agccaatgag aaaaaatata gtagcatgcc    3360
agatatctca ggattgtcta tgtccgcaag gaacatgcat ttaccaaaca acaagagtgg    3420
atactgggat ccgtcaagtg gaggaggagg gtatggtgcg tcttatggtc ggttaagcaa    3480
tgaatcatcg ttatattcta atttggggtc acgggtggga gtaccctcga cttatgatga    3540
catttctcaa tcaagaggag gctacagaga tgcctacagt ttgccacaga gtgcaacaac    3600
agggaccgga tcgcttttgg tccagacagc ctttgagcag tttggtgtag cggagaggaa    3660
tggtgctgtt ggtgaggagc tcaggaatag atcgaatccg atcaatatag acaacaacgc    3720
ttcttctaat gttgatgcag aggctaagct tcttcagtcg ttcaggcact gtattctaaa    3780
gcttattaaa cttgaaggat ccgagtggtt gttttggacaa agcgatggag ttgatgaaga    3840
actgattgac cgggtagctg cacgagagaa gtttatctat gaagctgaag ctcgagaaat    3900
aaaccaggtg ggtcacatgg gggagccact aatttcatcg gttcctaact gtggagatgg    3960
ttgcgtttgg agagctgatt tgattgtgag ctttggagtt tggtgcattc accgtgtcct    4020
tgacttgtct ctcatggaga gtcggcctga gctttgggga aagtacactt acgttctcaa    4080
ccgcctacag ggagtgattg atccggcgtt ctcaaagctg cggacaccaa tgacaccgtg    4140
cttttgcctt cagattccag cgagccacca gagagcgagt ccgacttcag ctaacggaat    4200
gttacctccg gctgcaaaac cggctaaagg caaatgcaca accgcagtca cacttcttga    4260
tctaatcaaa gacgttgaaa tggcaatctc ttgtagaaaa ggccgaaccg gtacagctgc    4320
aggtgatgtg gctttcccaa aggggaaaga gaatttggct tcggttttga agcggtataa    4380
acgtcggtta tcgaataaac cagtaggtat gaatcaggat ggacccggtt caagaaaaaa    4440
```

```
cgtgactgcg tacggatcat tgggttgaag aagaagaaca ttgtgagaaa tctcatgatc    4500
aaagtgacgt cgagagggaa gccgaagaat caaaactctc gcttttgatt gctcctctgc    4560
ttcgttaatt gtgtattaag aaaagaagaa aaaaaatgga ttttttgttgc ttcagaattt   4620 ttcgctcttt ttttcttaat ttggttgtaa tgttatgttt atatacatat atcatcatca    4680
taggaccata gctacaaacc gaatccggtt tgtgtaattc tatgcggaat cataaagaaa    4740
tcgtcg                                                               4746

<210> SEQ ID NO 11
<211> LENGTH: 6022
<212> TYPE: DNA
<213> ORGANISM: Arabidopsis thaliana

<400> SEQUENCE: 11
aggtggcacg agcacccata accttcagac ctatagatac aaatatgtat gtatacgttt      60
tttatatata aatattttat ataattgatt tttcgatctt cttttatctc tctctttcga     120
tggaactgag ctcttctct ctttcctctt cttttctctc tctatctcta tctctcgtag      180
cttgataaga gttctctctc tttgaagatc cgtttctctc tctctcactg agactattgt     240
tgttaggtca acttgcgatc atggcgattt cgaaggtgac ttctttcaaa aaccctaatc     300
ctctgttttt tttttttattt tgctgggggg ctttgtacgg actttcatgg gttttttgtag   360 cttttccctc ggcttttgcg caaatgagac tttctgggtt tttttttccag cttttttataa  420 tttcatcagg tggatcgaat tcgtagtttc agcttagatc tctctccctc ttcattatct     480
ggactttcca gacttggagt tcttcgggat tgttttcggt ttctgggttt tgtttttaatt    540 gcgagattta agcttttttc ttttttacta ctgtacttgg tttgtggttg accttttttt     600
tccttgaaga tctgaatgcg tagatcatac gggatctttg cattttttgtt gcttttcgtc    660 agcgttacga ttcttttagc ttcagtttag ttgaaatttg tatttttttt gagcttatct     720 tcttttttgtt gctgcttcat actaagatca attattgatt tgtaatacta ctgtatctga    780
agattttcac cataaaaaaa aaattcaggt ctgaagctga tttcgaatgg tttggagata     840
tccgtagtgg ttaagcatat ggaagtctat gttctgctct tggttgctct gttagggctt     900
cctccatttg gaccaactta gctgaatgtt gtatgatctc tctccttgaa gcagcaaata     960
agaagaaggt ctggtcctta acttaacatc tggttactag aggaaacttc agctattatt    1020
aggtaaagaa agactgtaca gagttgtata acaagtaagc gttagagtgg ctttgtttgc    1080
ctcggtgata gaagaaccga ctgattcgtt gttgtgtgtt agcttggag ggaatcagat     1140 ttcgcgaggg aaggtgtttt agatcaaatc tgtgaatttt actcaactga ggcttttagt    1200
gaaccacgac tgtagagttg accttgaatc ctactctgag taattatatt atcagataga    1260
tttaggatgg aagctgaaat tgtgaatgtg agacctcagc tagggtttat ccagagaatg    1320
gttcctgctc tacttcctgt cctttttggtt tctgtcggat atattgatcc cgggaaatgg   1380
gttgcaaata tcgaaggagg tgctcgtttc gggtatgact tggtggcaat tactctgctt    1440
ttcaattttg ccgccatctt atgccaatat gttgcagctc gcataagcgt tgtgactggt    1500
aaacacttgg ctcaggtaaa cattttttctg atctctaaag aacaaacttt ttaaaataac   1560
aaactgggct ctgtggttgt cttgtcactt tctcaaagtg gaattctact aaccaccttc    1620
tctatttttc taacatttta atgttcttta ctgggacaga tctgcaatga agaatatgac    1680
aagtggacgt gcatgttctt gggcattcag gcggagttct cagcaattct gctcgacctt    1740
accatggtag ttacttacaa tctttgctgt tcttaatttt tttattatgt gataaaattt     1800
```

```
tgattcctct gacttgagct tctctattat aaacaggttg tgggagttgc gcatgcactt    1860
aacctttttgt ttggggtgga gttatccact ggagtgtttt tggccgccat ggatgcgttt   1920
ttatttcctg ttttcgcctc tttccttgta tgactggtct tcctgtcttg ttttttttct   1980
ccacgttctt gaaatagcat tattggaaat tagctgacat gcatacaatt tctgacagga   2040
aaatggtatg gcaaatacag tatccattta ctctgcaggc ctggtattac ttctctatgt   2100
atctggcgtc ttgctgagtc agtctgagat cccactctct atgaatggag tgttaactcg   2160
gttaaatgga gagagcgcat tcgcactgat gggtcttctt ggcgcaagca tcgtccctca   2220
caatttttat atccattctt attttgctgg ggtaccttt ttctctttat atgtatctct    2280
cttttctgtt aagaagcaat aattatacta agcagtgaac gctctattac aggaaagtac   2340
atcttcgtct gatgtcgaca agagcagctt gtgtcaagac catttgttcg ccatctttgg   2400
tgtcttcagc ggactgtcac ttgtaaatta tgtattgatg aatgcagcag ctaatgtgtt   2460
tcacagtact ggccttgtgg tactgacttt tcacgatgcc ttgtcactaa tggagcaggt   2520
ttgttctgac ggttttatgt tcgtattagt ctataattca ttttaggga aaatgttcag    2580
aaatctctcg tgattattaa ttatcttgtt cttgattgtt gatcacaggt atttatgagt   2640
ccgctcattc cagtggtctt tttgatgctc ttgttcttct ctagtcaaat taccgcacta   2700
gcttgggctt tcggtggaga ggtcgtcctg catgacttcc tgaagataga aatacccgct   2760
tggcttcatc gtgctacaat cagaattctt gcagttgctc ctgcgcttta ttgtgtatgg   2820
acatctggtg cagacggaat ataccagtta cttatattca cccaggtctt ggtggcaatg   2880
atgcttcctt gctcggtaat accgcttttc cgcattgctt cgtcgagaca aatcatgggt   2940
gtccataaaa tccctcaggt tggcgagttc ctcgcactta aacgttttt gggatttctg    3000
gggttgaatg ttgttttttgt tgttgagatg gtatttggga gcagtgactg ggctggtggt  3060
ttgagatgga ataccgtgat gggcacctcg attcagtaca ccactctgct tgtatcgtca   3120
tgtgcatcct tatgcctgat actctggctg gcagccacgc cgctgaaatc tgcgagtaac   3180
agagcggaag ctcaaatatg gaacatggat gctcaaaatg cttatctta tccatctgtt    3240
caagaagagg aaattgaaag aacagaaaca aggaggaacg aagacgaatc aatagtgcgg   3300
ttggaaagca gggtaaagga tcagttggat actacgtctg ttactagctc ggtctatgat   3360
ttgccagaga acattctaat gacggatcaa gaaatccgtt cgagccctcc agaggaaaga   3420
gagttggatg taaagtactc tacctctcaa gttagtagtc ttaaggaaga ctctgatgta   3480
aaggaacagt ctgtattgca gtcaacagtg gttaatgagg tcagtgataa ggatctgatt   3540
gttgaaacaa agatggcgaa aattgaacca atgagtcctg tggagaagat tgttagcatg   3600
gagaataaca gcaagtttat tgaaaaggat gttgaagggg tttcatggga aacagaagaa   3660
gctaccaaag ctgctcctac aagcaacttt actgtcggat ctgatggtcc tccttcattc   3720
cgcagcttaa gtggggaagg gggaagtggg actggaagcc tttcacggtt gcaaggtttg   3780
ggacgtgctg cccggagaca cttatctgcg atccttgatg aatttggggg acatttatat   3840
gattttcatg ggcaattggt tgctgaagcc agggcaaaga aactagatca gctgtttggc   3900
actgatcaaa agtcagcctc ttctatgaaa gcagattcgt ttggaaaaga cattagcagt   3960
ggatattgca tgtcaccaac tgcgaaggga atggattcac agatgacttc aagtttatat   4020
gattcactga agcagcagag gacaccggga agtatcgatt cgttgtatgg attacaaaga   4080
ggttcgtcac cgtcaccgtt ggtcaaccgt atgcagatgt tgggtgcata tggtaacacc   4140
```

```
actaataata ataatgctta cgaattgagt gagagaagat actctagcct gcgtgctcca    4200
tcatcttcag agggttggga acaccaacaa ccagctacag ttcacggata ccagatgaag    4260
tcatatgtag acaatttggc aaaagaaagg cttgaagcct acaatcccg tggagagatc     4320 ccgacatcga gatctatggc gcttggtaca ttgagctata cacagcaact tgctttagcc    4380
ttgaaacaga agtcccagaa tggtctaacc cctggaccag ctcctgggtt tgagaatttt    4440
gctgggtcta gaagcatatc gcgacaatct gaaagatctt attacggtgt tccatcttct    4500
ggcaatactg atactgttgg cgcagcagta gccaatgaga aaaatatag tagcatgcca    4560 gatatctcag gattgtctat gtccgcaagg aacatgcatt taccaaacaa caagagtgga    4620
tactgggatc cgtcaagtgg aggaggaggg tatggtgcgt cttatggtcg gttaagcaat    4680
gaatcatcgt tatattctaa tttggggtca cgggtgggag taccctcgac ttatgatgac    4740
atttctcaat caagaggagg ctacagagat gcctacagtt tgccacagag tgcaacaaca    4800
gggaccggat cgctttggtc cagacagccc tttgagcagt ttggtgtagc ggagaggaat    4860
ggtgctgttg gtgaggagct caggaataga tcgaatccga tcaatataga caacaacgct    4920
tcttctaatg ttgatgcaga ggctaagctt cttcagtcgt tcaggcactg tattctaaag    4980
cttattaaac ttgaaggatc cgagtggttg tttggacaaa gcgatggagt tgatgaagaa    5040
ctgattgacc gggtagctgc acgagagaag tttatctatg aagctgaagc tcgagaaata    5100
aaccaggtgg gtcacatggg ggagccacta atttcatcgg ttcctaactg tggagatggt    5160
tgcgtttgga gagctgattt gattgtgagc tttggagttt ggtgcattca ccgtgtcctt    5220
gacttgtctc tcatggagag tcggcctgag ctttgggaa agtacactta cgttctcaac    5280
cgcctacagg taacaaaaac cgcagtagtt cattgaaaat cacagttttg cagtttgaaa    5340
atattgacat gtatggattt aaacagggag tgattgatcc ggcgttctca aagctgcgga    5400
caccaatgac accgtgcttt tgccttcaga ttccagcgag ccaccagaga gcgagtccga    5460
cttcagctaa cggaatgtta cctccggctg caaaaccggc taaaggcaaa tgcacaaccg    5520
cagtcacact tcttgatcta atcaaagacg ttgaaatggc aatctcttgt agaaaaggcc    5580
gaaccggtac agctgcaggt gatgtggctt tcccaaaggg gaaagagaat ttggcttcgg    5640
ttttgaagcg gtataaacgt cggttatcga ataaaccagt aggtatgaat caggatggac    5700
ccggttcaag aaaaaacgtg actgcgtacg gatcattggg ttgaagaaga agaacattgt    5760
gagaaatctc atgatcaaag tgacgtcgag agggaagccg aagaatcaaa actctcgctt    5820
ttgattgctc ctctgcttcg ttaattgtgt attaagaaaa gaagaaaaaa aatgattttt    5880
tgttgcttca gaattttttcg ctctttttt cttaatttgg ttgtaatgtt atgtttatat    5940
acatatatca tcatcatagg accatagcta caaaccgaat ccggtttgtg taattctatg    6000
cggaatcata agaaatcgt cg                                              6022
```

<210> SEQ ID NO 12
<211> LENGTH: 32
<212> TYPE: DNA
<213> ORGANISM: Artificial
<220> FEATURE:
<223> OTHER INFORMATION: oligonucleotide primer for PCR amplification of
     part of EIN2

<400> SEQUENCE: 12
gctggatccg gtaccttgaa tcctactctg ag                                    32

<210> SEQ ID NO 13

```
<211> LENGTH: 26
<212> TYPE: DNA
<213> ORGANISM: Artificial
<220> FEATURE:
<223> OTHER INFORMATION: oligonucleotide primer for PCR amplification of
      part of EIN2

<400> SEQUENCE: 13
gagatcgatc tcagactgac tcagca                                          26

<210> SEQ ID NO 14
<211> LENGTH: 368
<212> TYPE: DNA
<213> ORGANISM: Artificial
<220> FEATURE:
<223> OTHER INFORMATION: PSTVd variant

<400> SEQUENCE: 14
agatctcgga actaaactcg tggttcctgt ggttcacacc tgacctcctg acaagaaaag      60
aaaaaagaag gcggctcgga ggagcgcttc agggatcccc ggggaaacct ggagcgaact     120
ggcaaaaaag gacggtgggg agtgcccagc ggccgacagg agtaattccc gccaaacagg     180
gttttcacct ttcctttctt cgggtgtcct tcctcgcgcc cgcaggacca ccctggacc      240 cctttgcgct gtcgcttcgg ctactacccg gtggaaacaa ctgaagctcc cgagaaccgc     300
tttttctcta tcttacttgc tcgggcgagg gtgtttagcc cttggaaccg cagttggttc     360
ctagatct                                                             368

<210> SEQ ID NO 15
<211> LENGTH: 358
<212> TYPE: DNA
<213> ORGANISM: Artificial
<220> FEATURE:
<223> OTHER INFORMATION: PSTVd variant

<400> SEQUENCE: 15
agatctcgga actaaactcg tggttcctgt ggttcacacc tgacctcctg acaagaaaag      60
aaaaaagaag gcggctcgga ggagcgcttc agggatcccc ggggaaacct ggagcgaact     120
ggcaaaaagg acggtgggga gtgcccagcg gccgacagga gtaattcccg ccgaaacagg     180
gttttcaccc tttctttctt cgggtgtcct tcctcgcgcc cggaggacca ccctcgccc      240 cctttgcgct gtcgcttcgg ctactacccg gtggaaacaa ctgaagctcc cgagaaccgc     300
tttttctcta tcttacgagg gtgtttagcc cttggaaccg cagttggttc ctagatct      358
```

MODIFIED GENE-SILENCING RNA AND USES THEREOF

This application claims priority under 35 U.S.C. § 119 to U.S. Provisional Application No. 60/363,851 entitled MODIFIED GENE-SILENCING RNA AND USES THEREOF and filed on Mar. 14, 2002.

FIELD OF THE INVENTION

The present invention relates to methods for efficiently downregulating the expression of any gene of interest in eukaryotic cells and organisms. To this end, the invention provides modified antisense and sense RNA molecules, chimeric genes encoding such modified antisense or sense RNA molecules, and eukaryotic organisms such as plants, animals or fungi, yeasts or molds, comprising the modified antisense and/or sense RNA molecules and/or the chimeric genes encoding those RNA molecules.

BACKGROUND ART

Recently, it has been shown that introduction of double-stranded RNA (dsRNA) also called interfering RNA (RNAi), or hairpin RNA is an effective trigger for the induction of gene silencing in a large number of eukaryotic organisms, including animals, fungi, and plants.

Both the qualitative level of dsRNA-mediated gene silencing (i.e., the level of gene silencing within an organism) and the quantitative level (i.e., the number of organisms showing a significant level of gene silencing within a population) have proven superior to the more conventional antisense RNA or sense RNA mediated gene silencing methods.

For practical purposes, the production of antisense RNA molecules and chimeric genes encoding such antisense RNA is more straightforward than the production of dsRNA molecules or the genes encoding those RNA molecules. Indeed, the chimeric nucleic dsRNA molecules or the genes encoding those RNA molecules contain large, more or less perfect inverted repeat structures, and such structures tend to hamper the intact maintenance of these nucleic acids in intermediate prokaryotic cloning hosts. The methods and means to increase the efficiency of antisense-RNA mediated gene silencing as hereinafter described provide a solution to this problem as described in the different embodiments and claims.

U.S. Pat. No. 5,190,131 and EP 0 467 349 A1 describe methods and means to regulate or inhibit gene expression in a cell by incorporating into or associating with the genetic material of the cell a non-native nucleic acid sequence. The sequence is transcribed to produce an mRNA that is complementary to and capable of binding to the mRNA produced by the genetic material of that cell.

EP 0 223 399 A1 describes methods to effect useful somatic changes in plants by causing the transcription in the plant cells of negative RNA strands which are substantially complementary to a target RNA strand. The target RNA strand can be an mRNA transcript created in gene expression, a viral RNA, or other RNA present in the plant cells. The negative RNA strand is complementary to at least a portion of the target RNA strand to inhibit its activity in vivo.

EP 0 240 208 describes a method to regulate expression of genes encoded in plant cell genomes, achieved by integration of a gene under the transcriptional control of a promoter which is functional in the host. In this method, the transcribed strand of DNA is complementary to the strand of DNA that is transcribed from the endogenous gene(s) one wishes to regulate.

WO95/15394 and U.S. Pat. No. 5,908,779 describe a method and construct for regulating gene expression through inhibition by nuclear antisense RNA in mouse cells. The construct comprises a promoter, antisense sequences, and a cis-or trans-ribozyme that generates 3'-ends independently of the polyadenylation machinery and thereby inhibits the transport of the RNA molecule to the cytoplasm.

WO98/05770 discloses antisense RNA with special secondary structures such as $(GC)_n$-palindrome-$(GC)_n$, or $(AT)_n$- palindrome-$(AT)_n$, or $(CG)_n$-palindrome-$(CG)_n$, and the like.

WO 01/12824 discloses methods and means for reducing the phenotypic expression of a nucleic acid of interest in eukaryotic cells, particularly in plant cells, by providing aberrant, possibly unpolyadenylated, target-specific RNA to the nucleus of the host cell. Unpolyadenylated target-specific RNA may be provided by transcription of a chimeric gene comprising a promoter, a DNA region encoding the target-specific RNA, a self-splicing ribozyme and a DNA region involved in 3' end formation and polyadenylation.

WO 02/10365 provides a method for gene suppression in eukaryotes by transformation with a recombinant construct containing a promoter, at least one antisense and/or sense nucleotide sequence for the gene(s) to be suppressed, wherein the nucleus-to-cytoplasm transport of the transcription products of the construct is inhibited. In one embodiment, nucleus-to-cytoplasm transport is inhibited by the absence of a normal 3' UTR. The construct can optionally include at least one self-cleaving ribozyme. The construct can also optionally include sense and/or antisense sequences to multiple genes that are to be simultaneously downregulated using a single promoter. Also disclosed are vectors, plants, animals, seeds, gametes, and embryos containing the recombinant constructs.

Zhao et al., J. Gen. Virology, 82, 1491-1497 (2001) described the use of a vector based on Potato Virus X in a whole plant assay to demonstrate nuclear targeting of Potato spindle tuber viroid (PSTVd).

WO 02/00894 relates to gene silencing methods wherein the nucleic acid constructs comprise within the transcribed region a DNA sequence that consists of a stretch of T bases in the transcribed strand.

WO 02/00904 relates to gene silencing methods wherein nucleic acid constructs comprise (or encode) homology to at least one target mRNA expressed by a host, and in the proximity thereto, two complementary RNA regions which are unrelated to any endogenous RNA in the host.

SUMMARY OF THE INVENTION

In one embodiment of the present invention a method for downregulating the expression of a target gene in cells of a eukaryotic organisms is provided, comprising the steps of:
  providing the cells of the eukaryotic organism with a chimeric RNA molecule comprising:
    one or more target gene-specific regions comprising a nucleotide sequence of at least about 19 consecutive nucleotides, which has at least about 94% sequence identity with the complement of about 19 consecutive nucleotides from the nucleotide sequence of the target gene, operably linked to
    a largely double-stranded RNA region comprising a nuclear localization signal from a viroid of the Potato spindle tuber viroid (PSTVd)-type such as Potato Spindle tuber viroid, Citrus viroid species III, Citrus viroid species IV, Hop latent viroid, Australian grapevine viroid, T tinangaja viroid, Tomato apical stunt viroid, Coconut cadang-cadang viroid, *Citrus exocortis* viroid, Columnea latent viroid, Hop stunt viroid and Citrus bent leaf viroid or the largely double-stranded RNA region or a largely double-stranded RNA region comprising at least about 35 repeats of the trinucleotides CUG, CAG, GAC or GUC, such as between about 44 and about 2000 repeats of these trinucleotides; and identifying those eukaryotic organisms wherein the expression of the target gene is downregulated.

The chimeric RNA molecule may comprise an intron sequence. The viroids may have a genomic nucleotide sequence selected from the group consisting of SEQ ID NO: 3, SEQ ID NO: 4, SEQ ID NO: 5, SEQ ID NO: 6, SEQ ID NO: 7 and SEQ ID NO: 8. The eukaryotic organism may be a plant. Suitable plants include *Arabidopsis*, alfalfa, barley, bean, corn, cotton, flax, pea, rape, rice, rye, safflower, sorghum, soybean, sunflower, tobacco, wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon. The eukaryotic organism may also be a fungus, yeast or mold, or an animal such as a human, mammal, bird, fish, cattle, goat, pig, sheep, rodent, hamster, mouse, rat, guinea pig, rabbit, primate, nematode, shellfish, prawn, crab, lobster, insect, fruit fly, Coleopteran insect, Dipteran insect, Lepidopteran insect, or Homeopteran insect.

It is an object of the present invention to provide a chimeric RNA molecule for downregulating the expression of a target gene in a cell of a eukaryotic organism, comprising one target gene-specific region or multiple target gene-specific regions. A target gene-specific RNA region may comprise a nucleotide sequence of at least about 19 consecutive nucleotides having at least about 94% sequence identity with the complement of about 19 consecutive nucleotides from the nucleotide sequence of the target gene. The target gene-specific region may be operably linked to a largely double-stranded RNA region comprising a nuclear localization signal from a viroid of the Potato spindle tuber viroid (PSTVd)-type. Exemplary PSTVd-type viroids include Potato Spindle tuber viroid, Citrus viroid species III, Citrus viroid species IV, Hop latent viroid, Australian grapevine viroid, Tomato planta macho viroid, Coconut tinangaja viroid, Tomato apical stunt viroid, Coconut cadang-cadang viroid, *Citrus exocortis* viroid, Columnea latent viroid, Hop stunt viroid and Citrus bent leaf viroid. Alternatively, the target-gene-specific region may be operably linked to a largely double-stranded RNA region comprising at least about 35 repeats of the trinucleotide CUG, CAG, GAC, or GUC, such as between about 44 and about 2000 repeats of the trinucleotide CUG, CAG, GAC or GUC, wherein the chimeric RNA molecule, when provided to cells of the eukaryotic organism, downregulates the expression of the target gene.

It is another object of the invention to provide a chimeric DNA molecule for reduction of the expression of a target gene in a cell of a eukaryotic organism, comprising a promoter or promoter region capable of being recognized by RNA polymerases in the cells of the eukaryotic organism; operably linked to a DNA region, which when transcribed yields an RNA molecule, the RNA molecule comprising at least one target gene-specific region comprising a nucleotide sequence of at least about 19 consecutive nucleotides having at least about 94% sequence identity with the complement of about 19 consecutive nucleotides from the nucleotide sequence of the target gene; operably linked to a largely double-stranded RNA region comprising a nuclear localization signal from a viroid of the Potato spindle tuber viroid (PSTVd)-type such as Potato Spindle tuber viroid, Citrus viroid species III, Citrus viroid species IV, Hop latent viroid, Australian grapevine viroid, Tomato planta macho viroid, Coconut tinangaja viroid, Tomato apical stunt viroid, Coconut cadang-cadang viroid, *Citrus exocortis* viroid, Columnea latent viroid, Hop stunt viroid and Citrus bent leaf viroid, or at least about 35 repeats of the trinucleotide CUG, CAG, GAC or GUC, such as between about 44 and about 2000 repeats of the trinucleotide CUG, CAG, GAC or GUC; and optionally further comprising a transcription termination and polyadenylation signal operably linked to the DNA region encoding the RNA molecule, wherein the chimeric DNA molecule, when provided to cells of the eukaryotic organism, reduces the expression of the target gene.

Depending on the eukaryotic host organism, the promoter or promoter region may be a promoter or promoter region that functions in animals, a promoter or promoter region that functions in yeast, fungi or molds, or a plant-expressible promoter or promoter region. The promoter may also be a promoter or promoter region recognized by a single subunit bacteriophage RNA polymerase.

The invention also provides cells from a eukaryotic organism comprising chimeric DNA or RNA molecules according to the invention, as well as eukaryotic organisms comprising in their cells a chimeric DNA or RNA molecule according to the invention.

It is yet another object of the invention to provide the use of a chimeric RNA or DNA molecule according to the invention for reduction of the expression of a target gene in a cell of a eukaryotic organism.

The invention also provides a method for making a transgenic eukaryotic organism wherein expression of a target gene in cells of the organism is reduced, the method comprising the steps of:

providing a chimeric DNA molecule according to the invention to a cell or cells of the organism to make a transgenic cell or cells; and growing or regenerating a transgenic eukaryotic organism from the transgenic cell or cells.

The invention also provides a method for downregulating the expression of a target gene in cells of a eukaryotic organism, comprising the steps of providing the cells of the eukaryotic organism with a first and second chimeric RNA molecule, wherein the first chimeric RNA molecule comprises an antisense target gene-specific RNA region comprising a nucleotide sequence of at least about 19 consecutive nucleotides having at least about 94% sequence identity with the complement of about 19 consecutive nucleotides from the nucleotide sequence of the target gene;

the second chimeric RNA molecule comprises a sense target gene-specific RNA region comprising a nucleotide sequence of at least about 19 consecutive nucleotides having at least about 94% sequence identity to the complement of the first chimeric RNA molecule;

the first and second chimeric RNA are capable of base-pairing at least between the about 19 consecutive nucleotides of the first chimeric RNA and the about 19 consecutive nucleotides of the second chimeric RNA; and wherein either the first or the second chimeric RNA molecule comprises a largely double stranded RNA region operably linked to the antisense target-specific RNA region or to the sense target-specific RNA region; and identifying those eukaryotic organisms wherein the expression of the target gene is down regulated.

Both the first and second chimeric RNA molecule may comprise a largely double-stranded region.

It is another object of the invention to provide a cell from a eukaryotic organism (and eukaryotic organisms comprising such cells), comprising a first and second chimeric RNA molecule, wherein the first chimeric RNA molecule comprises an antisense target gene-specific RNA region comprising a nucleotide sequence of at least about 19 consecutive nucleotides having at least about 94% sequence identity with the complement of about 19 consecutive nucleotides from the nucleotide sequence of the target gene;

the second chimeric RNA molecule comprises a sense target gene-specific RNA region comprising a nucleotide sequence of at least about 19 consecutive nucleotides having at least about 94% sequence identity to the complement of the first chimeric RNA molecule;

the first and second chimeric RNA are capable of basepairing at least between the about 19 consecutive nucleotides of the first chimeric RNA and the about 19 consecutive nucleotides of the second chimeric RNA; and further wherein either the first or the second chimeric RNA molecule comprises a largely double stranded RNA region operably linked to the antisense target-specific RNA region or to the sense target-specific RNA region.

The invention further provides chimeric sense RNA molecules or chimeric DNA molecules encoding such chimeric sense RNA molecules for reduction of expression of a target gene in a cell of a eukaryotic organism in cooperation with a chimeric antisense RNA molecule. In this embodiment of the invention, the chimeric sense RNA molecule comprises a sense target gene-specific RNA region comprising a nucleotide sequence of at least about 19 consecutive nucleotides having at least about 94% sequence identity to the nucleotide of the target gene, operably linked to a largely double-stranded RNA region.

DETAILED DESCRIPTION OF THE DIFFERENT EMBODIMENTS

Figure 1:
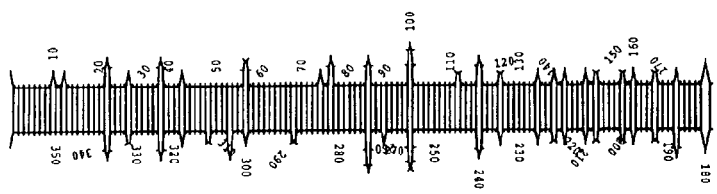
FIG. 1. Schematic representation of the secondary structure predicted using MFOLD software for different viroids of the PSTVd-type. A. Potato spindle tuber viroid; B. Australian grapevine viroid; C. Coconut tinangaja viroid; D. Tomato planta macho viroid; E. Hop latent viroid of thermomutant T229; F. Tomato apical stunt viroid.
Figure 1:
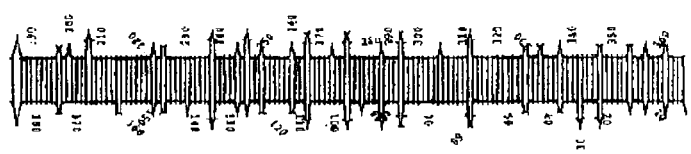
Figure 1:
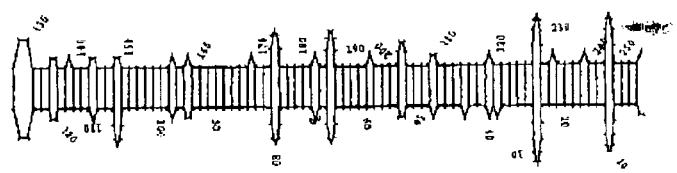
Figure 1:
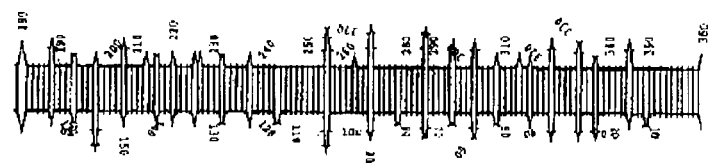
Figure 1:
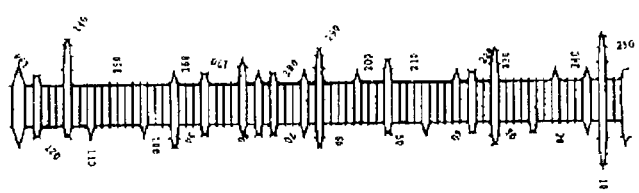
Figure 1:
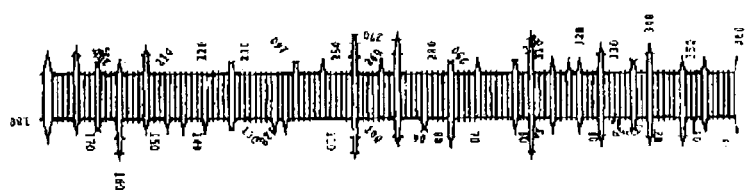
Figure 2:
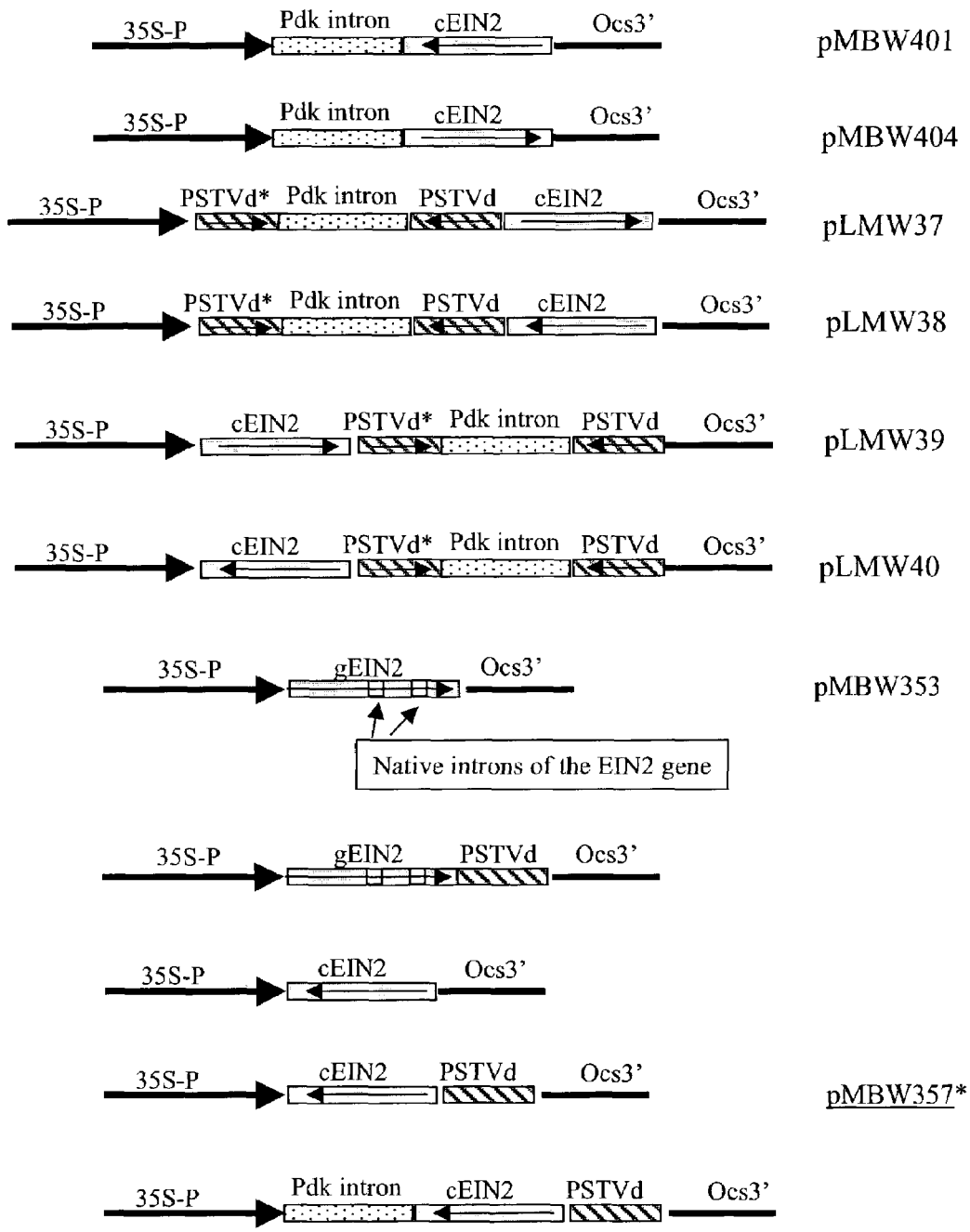
FIG. 2: schematic representation of the various chimeric gene constructs used in Examples 1 to 3, below. 35S-P: CaMV 35S promoter; Pdk intron: *Flaveria trinervia* pyruvate orthophosphate dikinase 2 intron 2; cEIN2: cDNA copy of the EIN2 gene from *Arabidopsis* (gene required for sensitivity to ethylene; Alonso et al. 1999 Science 284, 2148-2152) the orientation of this region with respect to the promoter is indicated by the arrow; gEIN2: genomic copy of the EIN2 gene from *Arabidopsis*; PSTVd: cDNA copy of the genome of potato spindle tuber viroid; PSTVd*: partial sequence from PSTVd from nucleotide 16 to nucleotide 355, cloned in inverse orientation with regard to the intact copy of PSTVd; OCS 3': 3' region of the octopine synthase gene from *Agrobacterium tumefaciens*.

Method and means are described herein for obtaining enhanced antisense RNA-mediated downregulation of gene expression. These methods and means are based upon the unexpected observation that operably linking the target gene-specific RNA sequence to a largely double-stranded RNA region, such as an RNA region comprising the nucleotide sequence of a Potato spindle tuber viroid genome, which in turn comprises a nuclear localization signal for the RNA in which it is embedded, when introduced into cells of a host organism, such as a plant cell, increased both the number of lines wherein gene expression of the target gene was downregulated, as well as the number of lines wherein gene expression of the target gene was significantly downregulated or even abolished.

Thus, in one embodiment of the invention, a method is provided for downregulating the expression of a target gene in cells of a eukaryotic organisms, comprising the steps of:

providing the cells of the eukaryotic organism with a chimeric RNA molecule wherein the RNA molecule comprises a target-gene specific RNA region comprising a nucleotide sequence of at least about 19 consecutive nucleotides having at least about 94% sequence identity with the complement of about 19 consecutive nucleotides from the nucleotide sequence of the target gene (the "antisense RNA"); operably linked to a largely double-stranded RNA region; and identifying those eukaryotic organisms wherein the expression of the target gene is downregulated.

"Chimeric gene" or "chimeric nucleic acid," as used herein, refers to any gene or any nucleic acid that is not normally found in a particular eukaryotic species or, alternatively, any gene in which the promoter is not associated in nature with part or all of the transcribed DNA region or with at least one other regulatory region of the gene.

As used herein, "antisense RNA" refers to RNA molecules that comprise a nucleotide sequence that is largely complementary to part of the nucleotide sequence of the biologically active RNA, usually but not exclusively mRNA, which is transcribed from the target gene.

The expression "target gene" is used herein to refer to any nucleic acid that is present in the eukaryotic cell and that is transcribed into a biologically active RNA. The target gene may be an endogenous gene, a transgene that was introduced through human intervention in the ancestors of the eukaryotic cell, or a gene introduced into the genome of the cell by infectious organisms such as, e.g., *Agrobacterium* strains or retroviruses. The target gene may also be of viral origin. The stretch of at least about 19 nucleotides may be selected from the promoter region, the 5'UTR, the coding region, or the 3'UTR.

"Gene expression" or "expression of a nucleic acid" is used herein to refer to the process wherein a gene or nucleic acid, when introduced in a suitable host cell, can be transcribed (or replicated) to yield an RNA, and/or translated to yield a polypeptide or protein in that host cell.

As used herein, "downregulation of gene expression" refers to the comparison of the expression of the target gene or nucleic acid of interest in the eukaryotic cell in the presence of the RNA or chimeric genes of the invention, to the expression of target gene or the nucleic acid of interest in the absence of the RNA or chimeric genes of the invention. The expression of the target gene in the presence of the chimeric RNA of the invention should thus be lower than the expression in its absence, so as to be only about 50% or about 25% or about 10% or about 5% of the phenotypic expression in absence of the chimeric RNA. For a number of applications, the expression should be completely inhibited for all practical purposes by the presence of the chimeric RNA or the chimeric gene encoding such an RNA.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region that is functionally or structurally defined may comprise additional DNA regions, etc.

It will thus be clear that the minimum nucleotide sequence of the antisense RNA of about 19 nt of the target-gene specific RNA region may be comprised within a larger RNA molecule, varying in size from about 19 nt to a length equal to the size of the target gene with a varying overall degree of sequence identity.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch 1970). Computer-assisted sequence alignment can be conveniently performed using standard software program such as GAP, which is part of the Wisconsin Package Version 10.1 (Genetics Computer Group, Madison, Wis., USA) using the default scoring matrix with a gap creation penalty of 50 and a gap extension penalty of 3. Sequences are indicated to be "essentially similar" when they have a sequence identity of at least about 75%, at least about 80%, at least about 85%, about 90%, about 95%, about 100%, or are identical. It is clear than when RNA sequences are essentially similar or have a certain lesser degree of sequence identity with DNA sequences, thymine (T) in the DNA sequence is considered equal to uracil (U) in the RNA sequence. Thus when it is stated in this application that a first sequence of 19 consecutive nucleotides has a 94% sequence identity to a second sequence of 19 nucleotides, this means that at least 18 of the 19 nucleotides of the first sequence are identical to 18 of the 19 nucleotides of the second sequence.

The mentioned antisense nucleotide regions may thus be about 21 nt, 50 nt, 100 nt, 200 nt, 300 nt, 500 nt, 1000 nt, 2000 nt or even about 5000 nt or larger in length, each having an overall sequence identity of about 40% or 50% or 60% or 70% or 80% or 90% or 100%. The longer the sequence, the less stringent is the requirement for the overall sequence identity.

Furthermore, multiple sequences with sequence identity to the complement of the nucleotide sequence of a target gene (multiple target-gene specific RNA regions) may be present within one RNA molecule. In addition, multiple sequences with sequence identity to the complement of the nucleotide sequences of several target genes may be present within one RNA molecule.

"Target gene-specific" is not to be interpreted in the sense that the chimeric nucleic acids according to the invention can only be used for downregulation of that specific target gene. Indeed, when sufficient homology exists between the target gene-specific RNA region and another gene, or when other genes share the same stretch of about 19 nucleotides (such as genes belonging to a "gene family"), expression of those other genes may also be downregulated.

As used herein, a "largely double-stranded RNA region" refers to an RNA molecule that is capable of folding into a rod-like structure by internal base pairing. The resulting rod-like structure does not comprise any stretch of 19 consecutive nucleotides having 94% sequence identity to the complement of another stretch of 19 other consecutive nucleotides within that RNA molecule, which are capable of forming a double-stranded region when the RNA molecule folds into a rod-like structure. In other words, the largely double-stranded RNA region, upon folding, does not contain a double-stranded RNA region of at least 19 bp with at most one mismatch in those 19 bp, at least not in the energetically most favorable rod-like confirmation. Non-limiting examples of such structures are represented in FIG. 1.

Although not intending to limit the invention to a specific mode of action, it is thought that such largely double stranded RNA regions are involved in the nuclear localization of the antisense RNA molecules with which they are associated. Consequently, the concentration of the antisense RNA molecules in the nucleus may be increased, allowing a more efficient formation of the formation of sequence-specific dsRNA formation by base pairing with the sense RNA corresponding to the antisense RNA.

As used herein, the phrase "Capable of folding into a rod-like structure" with regard to an RNA molecule refers to a secondary structure, which the RNA molecule may adapt by internal base pairing and which has the overall appearance of a long rod. The rod-like structure may comprise branches or bulges (where non-matching nucleotides bulge out from the overall structure) and may be part of a larger secondary structure (which may or may not be rod-like). Examples of RNA molecules capable of folding into a rod-like structure are represented in FIG. 1.

The specific secondary structure adapted will be determined by the free energy of the RNA molecule, and can be predicted for different situations using appropriate software, such as FOLDRNA (Zuker and Stiegler, 1981) or the MFOLD structure prediction package of GCG (Genetics Computing Group; Zuker 1989, Science 244, 48-52).

In one embodiment of the invention, the largely double-stranded RNA region operably linked to the antisense RNA molecule is a nuclear localization signal from a viroid of the PSTVd type, such as PSTVd (Potato spindle tuber viroid), capable of replicating in the nucleus of the host cell or host plant cell.

In one embodiment of the invention, the largely double stranded RNA region comprises the full length sequence of PSTVd strain RG1, which can conveniently be obtained by amplification from a cDNA copy of the RNA genome of the viroid using oligonucleotide primers with the nucleotide sequence

```
5'-cgcagatctcggaactaaactcgtggttc-3'   (SEQ ID NO: 1)
and

5'gcgagatctaggaaccaactgcggttc-3',     (SEQ ID NO: 2)
``` such as the nucleotide sequence represented in SEQ ID NO: 3.

It will be understood that for incorporation in an RNA molecule, an additional step is required to convert the DNA molecule in the corresponding RNA molecule. Such a conversion may be achieved by transcription, e.g., in vitro transcription using a single subunit bacteriophage RNA polymerase.

It will also be clear than when RNA sequences are said to be represented in an entry in the Sequence Listing or to be essentially similar or have a certain degree of sequence identity with DNA sequences represented in the Sequence Listing, reference is made to RNA sequences corresponding to the sequences in the entries, except that thymine (T) in the DNA sequence is replaced by uracil (U) in the RNA sequence. Whether the reference is to RNA or DNA sequence will be immediately apparent by the context.

Similar largely double-stranded RNA structures are also found within the genomes of other nuclear-replicating viroids of the PSTVd type (or group B according to the classification by Bussière et al. 1996), and these RNA sequences may be used to similar effect. Other nuclear-replicating viroids of the PSTVd group include Citrus viroid species III, Citrus viroid species IV, Coleus viroid, Hop latent viroid (SEQ ID NO: 7), Australian grapevine viroid (SEQ ID NO: 4), Tomato planta macho viroid (SEQ ID NO: 6), Coconut tinangaja viroid (SEQ ID NO: 5), Tomato apical stunt viroid (SEQ ID NO: 8), Coconut cadang-cadang viroid, *Citrus exocortis* viroid, Columnea latent viroid, Hop stunt viroid, and Citrus bent leaf viroid. These viroids are also characterized by the absence of self-splicing activity, which becomes apparent by the absence of catalytic motifs such as the hammerhead motif (Busière et al. Nuc. Acids Res. 24, 1793-1798, 1996). The longest stretch of perfect dsRNA structures among all the PSTVd-type of viroids is 11 base pairs in size. The mismatches are usually quite evenly distributed.

Nucleotide sequences for these viroids have been compiled in a database accessible via the worldwide web (http://www-.callisto.si.usherb.ca/~jpperra or http://nt.ars-grin.gov/subviral/) and include the following nucleotide sequences.

Potato spindle tuber viroid (PSTVd) (PSTVd.1 (Accession numbers: J02287(gb), M16826(gb), V01465(embl); 333351 (gi), 333352(gi) and 62283(gi)); PSTVd.2 (Accession numbers: M38345(gb), 333354(gi)); PSTVd.3 (Accession numbers: M36163(gb), 333356(gi)); PSTVd.4 (Accession numbers: M14814(gb), 333357(gi)); PSTVd.5 (strain: *S. commersonii*) (Accession numbers: M25199(gb), 333355(gi)); PSTVd.6 (strain: tomato cv. Rutgers, isolate: KF440-2) (Accession numbers: X58388(embl), 61366(gi)); PSTVd.7 (mild strain KF6-M) (Accession number: M88681 (gb), 333358(gi)); PSTVd.8 (strain Burdock) (Accession numbers: M88678(gb), 333360(gi)); PSTVd.9 (strain Wisconsin (WB)) (Accession numbers: M88677(gb), 333359(gi)); PSTVd.10 (strain PSTVd-N(Naaldwijk)) (Accession numbers: X17268(embl), 60649(gi));PSTVd.11 (mild strain variant A, WA-M isolate) (Accession numbers: X52036(embl), 61365(gi)); PSTVd.12 (mild strain, F-M isolate) (Accession numbers: X52037(embl), 61367(gi)); PSTVd.13 (intermediate-severe strain, F-IS isolate) (Accession numbers: X52039(embl), 61369(gi)); PSTVd.14 (severe-lethal strain, F-SL isolate) (Accession numbers: X52038(embl), 61368(gi)); PSTVd.15 (intermediate-severe strain, F88-IS isolate) as published in Herold, T et al., *Plant Mol. Biol.* 19, 329-333 (1992); PSTVd.16 (variant F88 or S88)(Accession numbers: X52040(embl), 61370(gi)); PSTVd.17 (individual isolate kf 5) (Accession numbers: M93685(gb), 333353(gi)); PSTVd.18 (isolate KF5) (Accession numbers: S54933(gb), 265593(gi)); PSTVd.19 (strain S-XII, variety s27) (Accession numbers: X76845(embl), 639994(gi)); PSTVd.20 (strain S-XIII, variety s23) (Accession numbers: X76846(embl), 639993(gi)); PSTVd.21 (strain M(mild)) (Accession numbers: X76844(embl), 639992(gi)); PSTVd.22 (strain I-818, variety I4) (Accession numbers: X76848(embl), 639991(gi)); PSTVd.23 (strain I-818, variety I3) (Accession numbers: X76847(embl), 639990(gi)); PSTVd.24 (strain PSTVd-341) (Accession numbers: Z34272(embl), 499191(gi)); PSTVd.25 (strain QF B) (Accession numbers: U23060(gb), 755586(gi)) PSTVd.26 (strain QF A) (Accession numbers: U23059(gb), 755585(gi)); PSTVd.27 (strain RG 1) (Accession numbers: U23058(gb), 755584(gi)); PSTVd.28 (Accession numbers: U51895(gb), 1272375(gi)); PSTVd.29(Potato spindle tuber viroid) (Accession numbers: X97387(embl), 1769438(gi)); PSTVd.30 (strain S27-VI-24) (Accession numbers: Y09382 (emb), 2154945(gi)); PSTVd.31 (strain S27-VI-19) (Accession numbers: Y09383(emb), 2154944(gi)); PSTVd.32 (strain SXIII) (Accession numbers: Y08852(emb), 2154943 (gi)); PSTVd.33 (strain S27-I-8) (Accession numbers: Y09381(emb), 2154942(gi)); PSTVd.34 (strain PSTV M-VI-15) (Accession numbers: Y09577(emb), 2154941(gi)); PSTVd.35 (strain PSTV M-I-40) (Accession numbers: Y09576(emb), 2154940(gi)); PSTVd.36 (strain PSTV M-I-17) (Accession numbers: Y09575(emb), 2154939(gi)); PSTVd.37 (strain PSTV M-I-10) (Accession numbers: Y09574(emb), 2154938(gi)); PSTVd.38 (variant I4-I-42) (Accession numbers: Y09889(emb), 2154937(gi)); PSTVd.39 (variant PSTVd I2-VI-27) (Accession numbers: Y09888(emb), 2154936(gi)); PSTVd.40 (variant PSTVd I2-VI-25) (Accession numbers: Y09887(emb), 2154935(gi)); PSTVd.41 (variant PSTVd I2-VI-16) (Accession numbers: Y09886(emb), 2154934(gi)); PSTVd.42 (variant PSTVd I4-I-10) (Accession numbers: Y09890(emb), 2154933(gi)); PSTVd.43 (variant PSTVd I2-I-14) (Accession numbers: Y09891(emb), 2154932(gi)); PSTVd.44 (isolate KF7) (Accession numbers: AJ007489(emb), 3367737(gi)); and PSTVd.45 (Accession numbers: AF369530, 14133876(gi).

Group III citrus viroid (CVd-III) (CVd-III.1 (Accession numbers: S76452(gb), 913161(gi)); CVd-III.2 (Australia New South Wales isolate) (Accession numbers: S75465(gb) and S76454(gb), 914078(gi) and 913162(gi)); CVd-III.3 (Accession numbers: AF123879, GI:7105753); CVd-III.4 (Accession numbers: AF123878, GI:7105752) CVd-III.5 (Accession numbers: AF123877, GI:7105751); CVd-III.6

(Accession numbers: AF123876, GI:7105750); CVd-III.7 (Accession numbers: AF123875, GI:7105749); CVd-III.8 (Accession numbers: AF123874, GI:7105748); CVd-III.9 (Accession numbers: AF123873, GI:7105747); CVd-III.10 (Accession numbers: AF123872, GI:7105746); CVd-III.11 (Accession numbers: AF123871, GI:7105745); CVd-III.12 (Accession numbers: AF123870, GI:7105744); CVd-III.13 (Accession numbers: AF123869, GI:7105743); CVd-III.14 (Accession numbers: AF123868, GI:7105742); CVd-III.15 (Accession numbers: AF123867, GI:7105741); CVd-III.16 (Accession numbers: AF123866, GI:7105740); CVd-III.17 (Accession numbers: AF123865, GI:7105739); CVd-III.18 (Accession numbers: AF123864, GI:7105738) CVd-III.19 (Accession numbers: AF123863, GI:7105737); CVd-III.20 (Accession numbers: AF123860, GI:7105736); CVd-III.21 (Accession numbers: AF123859, GI:7105735); CVd-III.22 (Accession numbers: AF123858, GI:7105734); CVd-III.23 (Accession numbers: AB054619, GI:13537479); CVd-III.24 (Accession numbers: AB054620, GI:13537480); CVd-III.25 (Accession numbers: AB054621, GI:13537481); CVd-III.26 (Accession numbers: AB054622, GI:13537482); CVd-III.27 (Accession numbers: AB054623, GI:13537483); CVd-III.28 (Accession numbers: AB054624, GI:13537484); CVd-III.29 (Accession numbers: AB054625, GI:13537485); CVd-III.30 (Accession numbers: AB054626, GI:13537486); CVd-III.31 (Accession numbers: AB054627, GI:13537487); CVd-III.32 (Accession numbers: AB054628, GI:13537488); CVd-III.33 (Accession numbers: AB054629, GI:13537489); CVd-III.34 (Accession numbers: AB054630, GI:13537490); CVd-III.35 (Accession numbers: AB054631, GI:13537491); CVd-III.36 (Accession numbers: AB054632, GI:13537492); CVd-III.37 (Accession numbers: AF416552, GI:15811643); CVd-III.38 (Accession numbers: AF416553, GI:15811644); CVd-III.39 (Accession numbers: AF416374, GI:15788948); and CVd-III.40 (Accession number: AF434680)).

Citrus viroid IV (CVdIV) (CVdIV.1 (Accession numbers: X14638(embl), 59042(gi)).

*Coleus blumei*-1 viroid (CbVd-1) (CbVd.1 (*Coleus blumei* viroid 1 (CbVd 1), strain cultivar Bienvenue, german isolate) (Accession numbers: X52960(embl), 58844(gi)); CbVd.2 (*Coleus* yellow viroid (CYVd), Brazilian isolate) (Accession numbers: X69293(embl), 59053(gi)); CbVd.3 (*Coleus blumei* viroid 1-RG stem-loop RNA.) (Accession numbers: X95291(embl), 1770104(gi)); and CbVd.4 (*Coleus blumei* viroid 1-RL RNA) (Accession numbers: X95366(embl), 1770106(gi)).

*Coleus blumei*-2 viroid (CbVd-2) (CbVd.1 (*Coleus blumei* viroid 2-RL RNA) (Accession numbers: X95365(embl), 1770107(gi)); and CbVd.2 (*Coleus blumei* viroid CbVd 4-1 RNA) (Accession numbers: X97202(embl), 1770109(gi))).

*Coleus blumei*-3 viroid (CbVd-3) (CbVd.1 (*Coleus blumei* viroid 3-RL) (Accession numbers: X95364(embl), 1770108 (gi)); CbVd.2 (*Coleus blumei* viroid 8 from the *Coleus blumei* cultivar 'Fairway Ruby') (Accession numbers: X57294 (embl),780766(gi)); and CbVd.3 (*Coleus blumei* viroid 3-FR stem-loop RNA, from the *Coleus blumei* cultivar 'Fairway Ruby') (Accession numbers: X95290(embl), 1770105(gi))).

Hop latent viroid (HLVd) (HLVd.1 (Accession numbers: X07397(embl), 60259(gi)); HLVd.2 ('thermomutant' T15) (Accession numbers: AJ290404(gb), 13872743(gi)); HLVd.3 ('thermomutant' T40)(Accession numbers: AJ290405.1(gb), 13872744(gi)); HLVd.4 ('thermomutant' T50)(Accession numbers: AJ290406(gb), 13872745(gi)); HLVd.5 ('thermomutant' T59)(Accession numbers: AJ290406(gb), 13872746 (gi)); HLVd.6 ('thermomutant' T61)(Accession numbers: AJ290408(gb) 13872747(gi)); HLVd.7 ('thermomutant' T75)(Accession numbers: AJ290409(gb), 13872748(gi)); HLVd.8 ('thermomutant' T92) (Accession numbers: AJ290410(gb), 13872749(gi)); HLVd.9 ('thermomutant' 218) (Accession numbers: AJ290411 (gb), 13872750(gi)); and HLVd.10 ('thermomutant' T229)(Accession numbers: AJ290412(gb), 13872751(gi))).

Australian grapevine viroid (AGVd) (AGVd.1 (Accession numbers: X17101(embl), 58574(gi))).

Tomato planta macho viroid (TPMVd) (TPMVd.1 (Accession numbers: K00817(gb))).

Coconut tinangaja viroid (CTiVd) (CTiVd.1 (Accession numbers: M20731(gb), 323414(gi))).

Tomato apical stunt viroid (TASVd) (TASVd.1 (Accession numbers K00818(gb), 335155(gi)); TASVd.2 (strain: indonesian) (Accession numbers: X06390(embl), 60650(gi)); and TASVd.3(Tomato apical stunt viroid-S stem-loop RNA.) (Accession numbers: X95293(embl), 1771788(gi))).

Cadang-cadang coconut viroid (CCCVd) (CCCVd.1 (isolate baao 54, ccRNA 1 fast) (Accession numbers: J02049(gb), 323275(gi)); CCCVd.2 (isolate baao 54, ccRNA 1 fast) (Accession numbers: J02050(gb), 323276(gi)); CCCVd.3 (isolate baao 54, ccRNA 1 slow) (Accession numbers: J02051 (gb), 323277(gi)); CCCVd.4 (isolates Ligao 14B, 620C, 191 D and T1, ccRNA 1 fast) (Haseloff et al. *Nature* 299, 316-321 (1982)) CCCVd.5 (isolates Ligao T1, ccRNA 1 slow) (Haseloff et al. *Nature* 299, 316-321 (1982)); CCCVd.6 (isolates Ligao 14B, ccRNA 1 slow) (Haseloff et al. *Nature* 299, 316-321 (1982)); and CCCVd.7 (isolate San Nasciso, ccRNA 1 slow) (Haseloff et al. *Nature* 299, 316-321 (1982))).

*Citrus exocortis* viroid (CEVd) (CEVd.1 (cev from gynura) (Accession numbers: J02053(gb), 323302(gi)); CEVd.2 (strain A) (Accession numbers: M34917(gb), 323305(gi)); CEVd.3 (strain de25)(Accession numbers: K00964(gb), 323303(gi)); CEVd.4 (strain de26) (Accession numbers: K00965(gb), 323304(gi)); CEVd.5 (CEV-JB) (Accession numbers: M30870(gb), 484119(gi)); CEVd.6 (CEV-JA) (Accession numbers: M30869(gb), 484118(gi)); CEVd.7 (Accession numbers: M30871(gb), 484117(gi)); CEVd.8 (CEV-A)(Accession numbers: M30868(gb), 484116(gi)); CEVd.9 (Visvader, J. E. and Symons, R. H. *Nucleic Acids Res*. 13, 2907-2920 (1985)) CEVd.10 (Visvader, J. E. and Symons, R. H. *Nucleic Acids Res*. 13, 2907-2920 (1985)); CEVd.11 (Visvader, J. E. and Symons, R. H. *Nucleic Acids Res*. 13, 2907-2920 (1985)); CEVd.12 (Visvader, J. E. and Symons, R. H. *Nucleic Acids Res*. 13, 2907-2920 (1985)); CEVd.13 (Visvader, J. E. and Symons, R. H. *Nucleic Acids Res*. 13, 2907-2920 (1985)); CEVd.14 (Visvader, J. E. and Symons, R. H. *Nucleic Acids Res*. 13, 2907-2920 (1985)); CEVd.15 (Visvader, J. E. and Symons, R. H. *Nucleic Acids Res*. 13, 2907-2920 (1985)); CEVd.16 (Visvader, J. E. and Symons, R. H. *Nucleic Acids Res*. 13, 2907-2920 (1985)); CEVd.17 (Visvader, J. E. and Symons, R. H. *Nucleic Acids Res*. 13, 2907-2920 (1985)); CEVd.18 (Visvader, J. E. and Symons, R. H. *Nucleic Acids Res*. 13, 2907-2920 (1985)); CEVd.19 (Visvader, J. E. and Symons, R. H. *Nucleic Acids Res*. 13, 2907-2920 (1985)); CEVd.20 (Visvader, J. E. and Symons, R. H. *Nucleic Acids Res*. 13, 2907-2920 (1985)); CEVd.21 (cev-j classe B) (Visvader, J. E. and Symons, R. H. *Nucleic Acids Res*. 13, 2907-2920 (1985)); CEVd.22 (Grapevine viroid (GV)) (Accession numbers: Y00328(embl), 60645(gi)); CEVd.23 (CEVd-t) (Accession numbers:

X53716(embl), 433503(gi)); CEVd.24 (CEVcIs, isolate tomato hybrid callus) (Accession numbers: S67446(gb), 141247(gi)); CEVd.25 (CEV D-92) (Accession numbers: S67442(gb), 141248(gi)); CEVd.26 (CEVt, isolate tomato hybrid) (Accession numbers: S67441(gb), 141246(gi)); CEVd.27 (CEVt, isolate tomato)(Accession numbers: S67440(gb), 141245(gi)); CEVd.28 (CEVg, isolate Gynura) (Accession numbers: S67438(gb), 141244(gi)); CEVd.29 (CEVc, isolate citron)(Accession numbers: S67437(gb), 141243(gi)); CEVd.30 (strain CEVd-225) (Accession numbers: U21126(gb), 710360(gi)); CEVd.31 (isolate broad bean, *Vicia faba* L.) (Accession numbers: S79831(gb), 1181910(gi)); CEVd.32 (variant obtained after inoculation tomato with cevd.31) (Fagoaga et al. *J. Gen. Virol.* 76, 2271-2277 (1995)); CEVd.33 (Fagoaga et al. *J. Gen. Virol.* 76, 2271-2277 (1995)); CEVd.34 (Accession numbers: AF298177, 15419885(gi)); CEVd.35 (Accession numbers: AF298178, 15419886(gi)); CEVd.36 (Accession: AF428058)(*Citrus exocortis* viroid isolate 205-E-1 Uy, complete genome.); CEVd.37 (Accession: AF428059) (*Citrus exocortis* viroid isolate 205-E-2 Uy, complete genome.); CEVd.38 (Accession: AF428060) (*Citrus exocortis* viroid isolate 205-E-5 Uy, complete genome.); CEVd.39 (Accession: AF428061) (*Citrus exocortis* viroid isolate 205-E-7 Uy, complete genome.); CEVd.40 (Accession: AF428062) (*Citrus exocortis* viroid isolate 54-E-1 Uy, complete genome.); CEVd.41 (Accession: AF428063) (*Citrus exocortis* viroid isolate 54-E-3 Uy, complete genome.); CEVd.42 (Accession: AF428064) (*Citrus exocortis* viroid isolate 54-E-18 Uy, complete genome.); and CEVd.43 (Accession: AF434678) (*Citrus exocortis* viroid, complete genome.)).

Columnea latent viroid (CLVd) (CLVd.1 (Accession numbers: X15663(embl), 58886(gi)); CLVd.2 (CLVd-N, individual isolate Nematanthus) (Accession numbers: M93686 (gb), 323335(gi)); and CLVd.3(Columnea latent viroid-B stem-loop RNA) (Accession numbers: X95292(embl), 1770174(gi))).

Citrus bent leaf viroid (CBLVd) (CBLVd.1 (CVd-Ib) (Accession numbers: M74065(gb), 323413(gi)); CBLVd.2 (strain CBLVd-225) (Accession numbers: U21125(gb), 710359(gi)); CBLVd.3 (viroid Ia genomic RNA, isolate: Jp) (Accession numbers: AB006734(dbj), 2815403(gi)); CBLVd.4 (viroid Ib genomic RNA, isolate: P2) (Accession numbers: AB006735(dbj), 2815401 (gi)); CBLVd.5 (viroid Ia genomic RNA) (Accession numbers: AB006736(dbj), 2815402(gi)); CBLVd.6 (Citrus Viroid Ia clone 17) (Accession numbers: AF040721(gb), 3273626(gi)); CBLVd.7 (Citrus Viroid Ia clone 18) (Accession numbers: AF040722(gb), 3273627(gi)); CBLVd.8 (Citrus bent leaf viroid isolate 201-1-1 Uy, complete genome.) (Accession: AF428052); CBLVd.9 (Citrus bent leaf viroid isolate 201-1-2 Uy, complete genome.) (Accession: AF428053); CBLVd.10 (Citrus bent leaf viroid isolate 201-1-5 Uy, complete genome.) (Accession: AF428054); CBLVd.11 (Citrus bent leaf viroid isolate 205-1-1 Uy, complete genome.) (Accession: AF428055); CBLVd.12 (Citrus bent leaf viroid isolate 205-1-3 Uy, complete genome.) (Accession: AF428056; and CBLVd.13 (Citrus bent leaf viroid isolate 205-1-4 Uy, complete genome.) (Accession: AF428057)).

Hop stunt viroid (HSVd) (HSVd.h1 (Japanese type strain) (Accession numbers: X00009(embl), 60684(gi)); HSVd.h2 (Japanese strain, variant 2) (Lee et al. *Nucleic Acids Res.* 16, 8708-8708 (1988)); HSVd.h3 (Korean strain) (Accession numbers: X12537(embl), 60421(gi)); HSVd.g1 (Grapevine viroid (GVVd), isolate SHV-g(GV)) (Accession numbers: M35717(gb), 325405(gi)); HSVd.g2 (strain: German cultivar Riesling) (Accession numbers: X06873(embl), 60422(gi)); HSVd.g3 (strain: isolated from Vitis vinifera Rootstock 5BB) (Accession numbers: X15330(embl), 60648(gi)); HSVd.g4 (isolate grapevine (HSVdg), variant Ia) (Accession numbers: X87924(embl), 897764(gi)); HSVd.g5 (isolate grapevine (HSVdg), variant Ib) (Accession numbers: X87923(embl), 897765(gi)); HSVd.g6 (isolate grapevine (HSVdg), variant Ic) (Accession numbers: X87925(embl), 897766(gi)); HSVd.g7 (isolate grapevine (HSVdg), variant Id)(Accession numbers: X87926(embl), 897767(gi)); HSVd.g8 (isolate grapevine (HSVdg), variant Ie) (Accession numbers: X87927 (embl), 897768(gi)); HSVd.g9 (isolate grapevine (HSVdg), variant IIa) (Accession numbers:X87928(embl), 897769(gi)); HSVd.cit1 (variant 1, isolate HSV-cit) (Accession numbers: X06718(embl), 60646(gi)); HSVd.cit2 (variant 2, isolate HSV-cit) (Accession numbers: X06719(embl), 60647(gi)); HSVd.cit3 (HSV.citrus) (Accession numbers: X13838(embl), 60418(gi)); HSVd.cit4(Accession numbers: U02527(gb), 409021(gi)); HSVd.cit5 (Hsu et al. *Virus Genes* 9, 193-195 (1995)); HSVd.cit6 cit5 (Hsu et al. *Virus Genes* 9, 193-195 (1995)); HSVd.cit7 (isolate CVd-IIa or E819) (Accession numbers: AF131248(gb)); HSVd.cit8 (isolate CVd-IIb or Ca902) (Accession numbers: AF131249(gb)); HSVd.cit9 (isolate CVd-IIc or Ca905) (Accession numbers: AF131250(gb)); HSVd.cit10 (isolate Ca903) (Accession numbers: AF131251 (gb)); HSVd.cit11 (isolate CA909) (Accession numbers: AF131252(gb)); HSVd.cit12 (cachexia isolate X-701-M) (Accession numbers: AF213483(gb), 12082502(gi)); HSVd.cit13 (cachexia isolate X-701-1) (Accession numbers: AF213484(gb), 12082503(gi)); HSVd.cit14 (cachexia isolate X-701-2) (Accession numbers: AF213485(gb), 12082504(gi)); HSVd.cit15 (cachexia isolate X-701-3) (Accession numbers: AF213486(gb), 12082505(gi)); HSVd.cit16 (cachexia isolate X-704-M) (Accession numbers: AF213487(gb), 12082506(gi)); HSVd.cit17 (cachexia isolate X-704-1) (Accession numbers: AF213488(gb), 12082507(gi)); HSVd.cit18 (cachexia isolate X-704-2) (Accession numbers: AF213489(gb), 12082508(gi)); HSVd.cit19 (cachexia isolate X-704-3) (Accession numbers: AF213490(gb), 12082509(gi)); HSVd.cit20 (cachexia isolate X-707-M) (Accession numbers: AF213491 (gb), 12082510(gi)); HSVd.cit21 (cachexia isolate X-707-1) (Accession numbers: AF213492(gb), 12082511 (gi)); HSVd.cit22 (cachexia isolate X-707-2) (Accession numbers: AF213493(gb), 12082512(gi)); HSVd.cit23 (cachexia isolate X-707-3) (Accession numbers: AF213494(gb), 12082513(gi)); HSVd.cit24 (cachexia isolate X-707-4) (Accession numbers: AF213495(gb), 12082514(gi)); HSVd.cit25 (cachexia isolate X-712-M) (Accession numbers: AF213496(gb), 12082515(gi)); HSVd.cit26 (cachexia isolate X-712-1) (Accession numbers: AF213497(gb), 12082516(gi)); HSVd.cit27 (cachexia isolate X-712-2) (Accession numbers: AF213498(gb), 12082517(gi)); HSVd.cit28 (cachexia isolate X-712-3) (Accession numbers: AF213499(gb), 12082518(gi)); HSVd.cit29 (cachexia isolate X-715-M) (Accession numbers: AF213500(gb), 12082519(gi)); HSVd.cit30 (cachexia isolate X-715-1) (Accession numbers: AF213501(gb), 12082520(gi)); HSVd.cit31 (cachexia isolate X-715-2) (Accession numbers: AF213502(gb), 12082521(gi)); HSVd.cit32 (CVd-IIa (117)) (Accession numbers: AF213503(gb), 12082522(gi)); HSVd.cit33 (isolate CVd-IIa 17uy) (Accession numbers: AF359276(gb), 13991644(gi)); HSVd.cit34 (isolate CVd-IIa 11 uy) (Accession numbers: AF359275(gb), 13991643(gi)); HSVd.cit35 (isolate CVd-IIa 10uy) (Accession numbers: AF359274(gb), 13991642(gi)); HSVd.cit36 (isolate CVd-Ib 10uy) (Accession numbers: AF359273(gb), 13991641(gi)); HSVd.cit37 (isolate CVd-Ib 5uy) (Accession numbers: AF359272(gb), 13991640(gi)); HSVd.cit38 (isolate CVd-Ib 3uy) (Accession numbers: AF359271(gb), 13991639(gi)); HSVd.cit39 (isolate CVd-Ib 2uy) (Accession numbers: AF359270(gb), 13991638(gi)); HSVd.cit40 (isolate CVd-IIa) (Accession numbers: X69519(embl), 2369773 (gi)); HSVd.cit41 (isolate CVd-IIb) (Accession numbers: X69518(embl),2369774(gi)); HSVd.cit42 (isolate CVd-IIa 54-2-1) (Accession numbers: AF416554,15811645(gi)); HSVd.cit43 (isolate CVd-IIa 54-2-2) (Accession numbers: AF416555, 15811646(gi)); HSVd.cit44 (isolate CVd-IIa 205-2-4) (Accession numbers: AF416556, 15811647(gi)); HSVd.cit45 (isolate CVd-IIa 205-2-1) (Accession numbers: AF416557, 15811648(gi)); HSVd.p1 (HSV-peach (A9)) (Accession numbers: D13765(dbj), 221254(gi)); HSVd.p2 (HSV-plum and HSV-peach (AF) isolate) (Accession numbers: D13764(dbj), 221255(gi)); HSVd.p3 (cv. Jeronimo J-16 from Spain) (Accession numbers: Y09352(embl),1684696 (gi)); HSVd.apr1 (cv. Rouge de Roussillon from France) (Accession numbers: Y08438(embl), 2462494(gi)); HSVd.apr2 (unknown cultivar from Spain) (Accession numbers: Y08437 (embl), 2462495(gi)); HSVd.apr3 (cv. Bulida from Spain) (Accession numbers: Y09345(embl),1684690 (gi)); HSVd.apr4 (cv. Bulida from Spain) (Accession numbers: Y09346(embl),1684691(gi)); HSVd.apr5 (cv. Bulida d'Arques from Spain) (Accession numbers: Y09344(embl), 1684692(gi)); HSVd.apr6 (cv. Pepito del Rubio from Spain) (Accession numbers:Y09347(embl), 1684697(gi)); HSVd.apr7 (cv. Pepito del Rubio from Spain) (Accession numbers: 09348(embl), 1684699(gi)); HSVd.apr8 (cv. Pepito del Rubio from Spain) (Accession numbers: Y09349(embl), 684698(gi)); HSVd.apr9 (cv. Canino from Morocco) (Accession numbers: AJ297825(gb), 10944963(gi)); HSVd.apr10 (cv. Canino from Morocco)(Accession numbers: AJ297826 (gb), 10944964(gi)); HSVd.apr11 (cv. Canino from Morocco) (Accession numbers: AJ297827(gb), 10944965(gi)); HSVd.apr12 (cv. Canino from Morocco) (Accession numbers: AJ297828(gb), 10944966(gi)); HSVd.apr13 (cv. Canino from Morocco) (Accession numbers: AJ297829(gb), 10944967(gi)); HSVd.apr14 (cv. Septik from Turkey) (Accession numbers: AJ297830(gb), 10944968 (gi)); HSVd.apr15 (cv. Monaco bello from Cyprus) (Accession numbers: AJ297831 (gb), 10944969(gi)); HSVd.apr16 (cv.Cafona from Cyprus) (Accession numbers: AJ297832 (gb), 10944970(gi)); HSVd.apr17 (cv.Cafona from Cyprus) (Accession numbers: AJ297833(gb), 10944971(gi)); HSVd.apr18 (cv.Boccuccia spinosa from Cyprus) (Accession numbers: AJ297834(gb), 10944972(gi)); HSVd.apr19 (cv. Palumella from Cyprus) (Accession numbers: AJ297835 (gb), 10944973(gi)); HSVd.apr20 (cv. Palumella from Cyprus) (Accession numbers: AJ297836(gb), 10944974(gi)); HSVd.apr21 (cv.Canino from Cyprus) (Accession numbers: AJ297837(gb), 10944975(gi)); HSVd.apr22 (cv.Kolioponlou from Greece) (Accession numbers: AJ297838(gb), 10944976(gi)); HSVd.apr23 (cv. Bebecou Paros from Greece) (Accession numbers: AJ297839(gb), 10944977(gi)); HSVd.apr24 (cv. Bebecou Paros from Greece) (Accession numbers: AJ297840(gb), 10944978(gi)); HSVd.c1 (Cucumber pale fruit viroid (CPFVd), isolate HSV-cucumber) (Accession numbers: X00524(embl), 60644(gi)); HSVd.c2 (Cucumber pale fruit viroid (CPFVd)) (Accession numbers: X07405(embl), 59015(gi)); HSVd.alm1 (Accession numbers: AJOL 1813(emb), 3738118(gi)); HSVd.alm2 (Accession numbers: AJOL 1814(emb), 3738119(gi)); and HSVd. Citrus viroid II, complete genome (Accession number: AF434679)]. All the above nucleotide sequences are herein incorporated by reference.

As will be immediately apparent from the above list, viroids are extremely prone to sequence variations. Such natural variants can be used for the currently described methods and means, particularly if they retain the capacity to be transported to the nucleus, together with any operably linked RNA.

In addition to the natural variations in viroid nucleotide sequences, variants may be obtained by substitution, deletion or addition of particular nucleotides. Such variants may be suitable for the currently described methods and means, particularly if they retain the capacity to be transported to the nucleus, together with any operably linked RNA.

Further, smaller RNA regions derived from the viroid nucleotide sequences, and variants thereof, that are capable of being transported to the nucleus together with any operably linked RNA, can be used for the current invention.

The capacity of both smaller regions and variants derived from viroid nucleotide sequences to be transported to the nucleus of a host cell, such as a plant cell, can be determined using the assay described by Zhou et al. 2001, J. Gen Virology, 82, 1491-1497. Briefly, the assay comprises introducing a marker-coding region, such as GFP, comprising an intervening sequence in the coding region of the marker gene, into the host cell by means of a viral RNA vector that replicates in the cytoplasm of the host cell. When a functional nuclear localization signal is introduced (conveniently inserted in the intervening sequence), the viral RNA vector comprising the marker gene is imported into the nucleus, where the intron can be removed and the spliced RNA returned to the cytoplasm. The spliced RNA can be detected by the translation into GFP protein, as well as by RNA analysis methods (e.g. RT-PCR) to confirm the absence of the intron from the spliced RNA molecules.

The human hepatitis delta RNA may also be used according to the invention. The human hepatitis delta RNA is a 1700 nt single-stranded circular RNA, which is very similar to the viroids of the PSTVd-type in that is localized in the nucleus, forming rod-like structures.

In another embodiment of the invention, the largely double-stranded RNA region comprises CUG, CAG, GAC or GUC repeats. As used herein "trinucleotide repeats or CUG, CAG, GAC or GUC repeats" are RNA molecules comprising a number of CUG, CAG, GAC or GUC trinucleotides. The CUG trinucleotides may be repeated without intervening sequences, although short regions of 1 to about 20 to about 30 nucleotides not consisting of CUG trinucleotides may be present occasionally between the CUG trinucleotide repeats. The CUG repeats may comprise a number of CUG trinucleotide exceeding about 35 copies or about 44 copies, such as any number between about 50 and about 2000 copies. In particular embodiments, the copy number of the CUG triplets will not exceed about 100 or about 150. It is expected that CAG, GAC or GUC repeats may be used to similar effect.

Without intending to limit the invention to a particular mode of action, it is taught that such trinucleotide repeats form rod-like structures (by imperfect base-pairing) which function as nuclear retention signal, possibly by sterically blocking RNA export through nuclear pores, as well as activate double stranded RNA dependent protein kinase PKR (Davis et al, 1997 Proc. Natl. Acad. Sci. 94, 7388-7393; Tian et al. 2000 RNA 6, 79-87; Koch and Lefert 1998 J. Theor. Biol. 192, 505-514).

CUG repeats may be particularly suited to increase the efficiency of antisense-mediated gene silencing when the RNA molecules comprising such CUG repeats can be delivered to the nucleus of the host cell, e.g., through transcription of a chimeric gene encoding such RNA, as hereinafter described.

Although the largely double-stranded RNA region such as the PSTVd-type viroid derived nuclear location signals or the trinucleotide repeats can be located at the 3' end of the target specific antisense RNA, it is expected that the location of the largely double-stranded RNA is of little importance. Hence, largely double-stranded RNA regions may also be located at the 5' end of the RNA molecule, at the 3' end, or even in the middle of such an RNA molecule.

It was also unexpectedly found that the efficiency of antisense-mediated downregulation of gene expression, wherein the antisense RNA was operably linked to a largely double-stranded RNA region, could be further enhanced by inclusion of an intron sequence in the RNA molecule provided to the host cell.

Again, the location of the intron in the RNA molecule with respect to both the target specific nucleotide sequence as well as the largely double-stranded RNA region is expected to have little effect on efficiency. In fact, it is expected that the largely double-stranded RNA region may be located within the intron sequence.

As used herein, an "intron" or intervening sequence is used to refer to a DNA region within a larger transcribed DNA region, which is transcribed in the nucleus to yield an RNA region which is part of a larger RNA, however, the RNA region corresponding to intro sequence is removed from the larger RNA when transferred to the cytoplasm. The corresponding RNA is also referred to as an intron or intervening sequence. Intron sequences are flanked by splice sites, and synthetic introns may be made by joining appropriate splice sites to any sequence having an appropriate branching point. Introns or intervening sequences that are located in 5'UTR, coding region, or 3'UTR may be used.

Intervening sequences or introns may be capable of being spliced in the eukaryotic host cells, although the presence of intervening sequences which can no longer be spliced, e.g. because their guide sequences have been altered or mutated, may even further increase the efficiency of the chimeric RNA molecules to downregulate the expression of a target gene. In one embodiment of the invention, the intron is essentially identical in sequence to the *Flaveria trinervia* pyruvate orthophosphate dikinase 2 intron 2 (pdk2 intron) and may comprise the sequence of SEQ ID No. 9. Other examples of plant introns include the catalase intron from Castor bean (Accession number AF274974), the Delta12 desaturase (Fad2) intron from cotton (Accession number AF331163), the Delta 12 desaturase (Fad2) intron from *Arabidopsis* (Accession number AC069473), the Ubiquitin intron from maize (Accession number S94464), and the actin intron from rice. Other examples of mammalian virus introns include the intron from SV40. Examples of fungal introns include the intron from the triose phosphate isomerase gene from *Aspergillus*.

It was also unexpectedly found that further introduction of a sense RNA molecule with a target gene-specific region corresponding to the target gene-specific region of the antisense RNA molecule already present in the cell of the eukaryotic organism, further increased the efficiency of the downregulation of the expression of the target gene. The same efficiency of downregulation of the expression of a target gene could be observed if the sense RNA molecule was provided with a largely double-stranded RNA region as herein described. Sense RNA was provided to a cell of a eukaryotic host organism simultaneously with antisense RNA capable of forming a double-stranded region by basepairing with the sense RNA.

Thus, in another embodiment of the invention a method is provided for downregulating the expression of a target gene in cells of a eukaryotic organisms, comprising the steps of providing the cells of the eukaryotic organism with a first and second chimeric RNA molecule, wherein the first chimeric RNA molecule comprises an antisense target-gene specific RNA region comprising a nucleotide sequence of at least about 19 consecutive nucleotides having at least about 94% sequence identity with the complement of about 19 consecutive nucleotides from the nucleotide sequence of the target gene;

the second chimeric RNA molecule comprises a sense target gene-specific RNA region comprising a nucleotide sequence of at least about 19 consecutive nucleotides having at least about 94% sequence identity to the complement of the first chimeric RNA molecule;

the first and second chimeric RNA are capable of basepairing at least between the about 19 consecutive nucleotides of the first chimeric RNA and the about 19 consecutive nucleotides of the second chimeric RNA; and either the first or the second chimeric RNA molecule comprises a largely double-stranded RNA region operably linked to the antisense target-specific RNA region or to the sense target-specific RNA region; and identifying those eukaryotic organisms wherein the expression of the target gene is downregulated.

In another specific embodiment, both the first and second chimeric RNA molecule comprise a largely double-stranded region. Specific embodiments of the largely double-stranded RNA region and target gene-specific antisense RNA are described elsewhere herein. Specific embodiments for the sense RNA region are similar to the specific embodiments for the antisense RNA region.

Conveniently, the antisense or sense RNA molecules comprising a largely double stranded RNA region as herein described may be provided to the eukaryotic host cell or organism by introduction and possible integration of a chimeric gene, transcription of which yields such an antisense or sense RNA. Thus the invention is also aimed at providing such a chimeric gene comprising a promoter or a promoter region which is capable of being expressed in cells of the eukaryotic organism of interest; operably linked to a DNA region which when transcribed yields an antisense RNA molecule comprising a target gene-specific antisense nucleotide sequence of at least about 19 consecutive nucleotides having at least about 94% sequence identity with the complement of about 19 consecutive nucleotides from the nucleotide sequence of the target gene; or a target gene-specific sense nucleotide sequence of at least about 19 consecutive nucleotides having at least about 94% sequence identity with about 19 consecutive nucleotides from the nucleotide sequence of the target gene;

operably linked to a largely double-stranded RNA region as herein described; and optionally a transcription termination and polyadenylation region suitable for the eukaryotic cell of choice.

As used herein, the term "promoter" denotes any DNA that is recognized and bound (directly or indirectly) by a DNA-dependent RNA polymerase during initiation of transcription. A promoter includes the transcription initiation site, and binding sites for transcription initiation factors and RNA polymerase, and can comprise various other sites (e.g., enhancers), at which gene expression regulatory proteins may bind.

The term "regulatory region", as used herein, means any DNA that is involved in driving transcription and controlling (i.e., regulating) the timing and level of transcription of a given DNA sequence, such as a DNA coding for a protein or polypeptide. For example, a "5' regulatory region" (or "promoter region") is a DNA sequence located upstream (i.e., 5') of a coding sequence and which comprises the promoter and the 5'-untranslated leader sequence. A "3' regulatory region" is a DNA sequence located downstream (i.e., 3') of the coding sequence and which comprises suitable transcription termination (and/or regulation) signals, including one or more polyadenylation signals.

In one embodiment of the invention, the promoter is a constitutive promoter. In another embodiment of the invention, the promoter activity is enhanced by external or internal stimuli (inducible promoter), such as but not limited to hormones, chemical compounds, mechanical impulses, and abiotic or biotic stress conditions. The activity of the promoter may also be regulated in a temporal or spatial manner (e.g., tissue-specific promoters; developmentally regulated promoters).

In a particular embodiment of the invention, the promoter is a plant-expressible promoter. As used herein, the term "plant-expressible promoter" means a DNA sequence that is capable of initiating and/or controlling transcription in a plant cell. This includes not only promoters of plant origin, but also any promoter of non-plant origin that is capable of directing transcription in a plant cell. Examples of such non-plant promoters include certain promoters of viral or bacterial origin, such as the CaMV35S (Hapster et al., 1988), the subterranean clover virus promoter No 4 or No 7 (WO9606932), or T-DNA gene promoters. Also included within the definition of plant-expressible promoters are tissue-specific or organ-specific promoters. Exemplary tissue- or organ-specific promoters include seed-specific promoters (e.g., WO89/03887), organ-primordia specific promoters (An et al., 1996), stem-specific promoters (Keller et al., 1988), leaf specific promoters (Hudspeth et al., 1989), mesophyl-specific promoters (such as the light-inducible Rubisco promoters), root-specific promoters (Keller et al., 1989), tuber-specific promoters (Keil et al., 1989), vascular tissue specific promoters (Peleman et al., 1989), stamen-selective promoters (WO 89/10396, WO 92/13956), dehiscence zone specific promoters (WO 97/13865), and the like.

In another embodiment of the invention, the promoter is a fungus-expressible promoter. As used herein, the term "fungus-expressible promoter" means a DNA sequence that is capable of initiating and/or controlling transcription in a fungal cell. Exemplary fungus-expressible promoters include the *A. nidulans* trpC gene promoter, or the inducible *S. cerevisiae* GAL4 promoter.

In yet another embodiment of the invention, the promoter is an animal-expressible promoter. As used herein, the term "animal-expressible promoter" means a DNA sequence that is capable of initiating and/or controlling transcription in an animal cell. Exemplary animal-expressible promoters include SV40 late and early promoters, cytomegalovirus CMV-IE promoters, RSV-LTR promoter, SCSV promoter, SCBV promoter, and the like.

The antisense or sense RNA molecules useful for the invention may also be produced by in vitro transcription. To this end, the promoter of the chimeric genes according to the invention may be a promoter recognized by a bacteriophage single subunit RNA polymerase, such as the promoters recognized by bacteriophage single subunit RNA polymerase such as the RNA polymerases derived from the *E. coli* phages T7, T3, ϕI, ϕII, W31, H, Y, A1, 122, cro, C21, C22, and C2; *Pseudomonas putida* phage gh-1; *Salmonella typhimurium* phage SP6; *Serratia marcescens* phage IV; *Citrobacter* phage ViIII; and *Klebsiella* phage No.11 (Hausmann, Current Topics in Microbiology and Immunology, 75: 77-109 (1976); Korsten et al., J. Gen Virol. 43: 57-73 (1975); Dunn et al., Nature New Biology, 230: 94-96 (1971); Towle et al., J. Biol. Chem. 250:1723-1733(1975); Butler and Chamberlin, J. Biol. Chem., 257: 5772-5778 (1982)). Examples of such promoters are a T3 RNA polymerase specific promoter and a T7 RNA polymerase specific promoter, respectively. A T3 promoter to be used as a first promoter in the CIG can be any promoter of the T3 genes as described by McGraw et al, Nucl. Acid Res. 13: 6753-6766 (1985). Alternatively, a T3 promoter may be a T7 promoter which is modified at nucleotide positions −10, −11 and −12 in order to be recognized by T3 RNA polymerase (Klement et al., J. Mol. Biol. 215, 21-29(1990). A suitable T3 promoter is the promoter having the "consensus" sequence for a T3 promoter, as described in U.S. Pat. No. 5,037,745. A T7 promoter which may be used according to the invention, in combination with T7 RNA polymerase, may comprise a promoter of one of the T7 genes as described by Dunn and Studier, J. Mol. Biol. 166: 477-535 (1983). A suitable T7 promoter may comprise the "consensus" sequence for a T7 promoter, as described by Dunn and Studier (supra).

The antisense or sense RNA can be produced in large amounts by contacting the acceptor vector DNA with the appropriate bacteriophage single subunit RNA polymerase under conditions well known to the skilled artisan. The so-produced antisense or sense RNA can then be used for delivery into cells prone to gene silencing, such as plant cells, fungal cells or animal cells. Antisense RNA may be introduced in animal cells via liposomes or other transfection agents (e.g., Clonfection transfection reagent, or the CalPhos Mammalian transfection kit from ClonTech) and could be used for methods of treatment of animals, including humans, by silencing the appropriate target genes. Antisense or sense RNA can be introduced into the cell by whatever means is deemed suitable by the skilled artisan. For example, the antisense or sense RNA may be administered by microinjection, bombardment by particles covered by the antisense or sense RNA, soaking the cell or organisms in a solution of the antisense or sense RNA, electroporation of cell membranes in the presence of antisense or sense RNA, liposome mediated delivery of antisense or sense RNA and transfection mediated by chemicals such as calcium phosphate, viral infection, transformation and the like.

The antisense or sense RNA may be introduced along with components that enhance RNA uptake by the cell, stabilize the annealed strands, or otherwise increase inhibition of the target gene. In the case of a whole animal, the antisense or sense RNA is conveniently introduced by injection or perfusion into a cavity or interstitial space of an organism, or systemically via oral, topical, parenteral (including subcutaneous, intramuscular or intravenous administration), vaginal, rectal, intranasal, ophthalmic, or intraperitoneal administration. The antisense or sense RNA may also be administered via an implantable extended release device.

The chimeric genes according to the invention capable of producing antisense or sense RNA may also be equipped with any prokaryotic promoter suitable for expression of the antisense or sense RNA in a particular prokaryotic host. The prokaryotic host can be used as a source of antisense and/or sense RNA, e.g. by feeding it to an animal, such as a nematode or an insect, in which the silencing of the target gene is envisioned and monitored by reduction of the expression of the reporter gene. In this case, it will be clear that the target gene and reporter genes should be genes present in the cells of the target eukaryotic organism, and not in the prokaryotic host organism.

The antisense and sense RNA according to the invention, or chimeric genes capable of yielding such antisense or sense RNA molecules, can thus be produced in one host organism, administered to another (target) organism (e.g. through feeding, orally administering, as a naked DNA or RNA molecule or encapsulated in a liposome, in a virus particle or attenuated virus particle, or on an inert particle, etc.) and effect reduction of gene expression in the target gene or genes in another organism.

Suitable transcription termination and polyadenylation region include but are not limited to the SV40 polyadenylation signal, the HSV TK polyadenylation signal, the nopaline synthase gene terminator of *Agrobacterium tumefaciens*, the terminator of the CaMV 35S transcript, terminators of the subterranean stunt clover virus, the terminator of the *Aspergillus nidulans* trpC gene and the like.

The invention also supplies methods for providing antisense and sense RNA molecules, which may be obtained by transcription from these chimeric genes, and which are useful for the methods according to the invention.

The present invention also provides eukaryotic cells, and eukaryotic organisms, containing the antisense RNA molecules of the invention, or containing the chimeric genes capable of producing the antisense RNA molecules of the invention. In one embodiment, the chimeric genes are stably integrated in the genome of the cells of the eukaryotic organism.

The present invention also provides eukaryotic cells and eukaryotic organisms simultaneously containing sense and antisense RNA molecules of which one or both of the RNA molecules comprise a largely double-stranded RNA region, or chimeric genes encoding such RNA molecules.

In another embodiment, the chimeric genes of the invention may be provided on a DNA molecule capable of autonomously replicating in the cells of the eukaryotic organism, such as, e.g., viral vectors. The chimeric gene or the antisense or sense RNA may also be provided transiently to the cells of the eukaryotic organism.

Introduction of chimeric genes (or RNA molecules) into the host cell can be accomplished by a variety of methods including calcium phosphate transfection, DEAE-dextran mediated transfection, electroporation, microprojectile bombardment, microinjection into nuclei and the like.

Methods for the introduction of chimeric genes into plants are well known in the art and include *Agrobacterium*-mediated transformation, particle gun delivery, microinjection, electroporation of intact cells, polyethylene glycol-mediated protoplast transformation, electroporation of protoplasts, liposome-mediated transformation, silicon-whiskers mediated transformation, etc. The transformed cells obtained in this way may then be regenerated into mature fertile plants.

Transgenic animals can be produced by the injection of the chimeric genes into the pronucleus of a fertilized oocyte, by transplantation of cells, such as undifferentiated cells into a developing embryo to produce a chimeric embryo, transplantation of a nucleus from a recombinant cell into an enucleated embryo or activated oocyte and the like. Methods for the production of transgenic animals are well established in the art and include U.S. Pat. No. 4,873,191; Rudolph et al. 1999 (Trends Biotechnology 17:367-374); Dalrymple et al. (1998) Biotechnol. Genet. Eng. Rev. 15: 33-49; Colman (1998) Bioch. Soc. Symp. 63: 141-147; Wilmut et al. (1997) Nature 385: 810-813, Wilmute et al. (1998) Reprod. Fertil. Dev. 10: 639-643; Perry et al. (1993) Transgenic Res. 2: 125-133; Hogan et al. Manipulating the Mouse Embryo, $2^{nd}$ ed. Cold Spring Harbor Laboratory press, 1994 and references cited therein.

Gametes, seeds, embryos, progeny, and hybrids of plants or animals comprising the chimeric genes of the present invention, which are produced by traditional breeding methods are also included within the scope of the present invention.

The methods and means described herein can be applied to any eukaryotic organism in which gene silencing takes place. Such organisms include, but are not limited to, plants (such as corn, wheat, potato, sunflower, turf grasses, barley, rye, soybeans, tobacco, trees, flax, palm trees, peanuts, beans, etc.); invertebrate animals (such as insects, shellfish, mollusks, crustaceans such as crabs, lobsters and prawns) vertebrate animals (fish, birds, mammals, humans); yeast; and fungi, amongst others.

The following non-limiting Examples describe method and means for enhanced antisense RNA mediated silencing of the expression of a target gene in eukaryotic cell or combined sense/antisense RNA mediated target gene silencing.

Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Other references for standard molecular biology techniques include Sambrook and Russell (2001) *Molecular Cloning: A Laboratory Manual*, Third Edition, Cold Spring Harbor Laboratory Press, NY, Volumes I and II of Brown (1998) *Molecular Biology LabFax*, Second Edition, Academic Press (UK). Standard materials and methods for polymerase chain reactions can be found in Dieffenbach and Dveksler (1995) *PCR Primer: A Laboratory Manual*, Cold Spring Harbor Laboratory Press, and in McPherson at al. (2000) *PCR—Basics: From Background to Bench*, First Edition, Springer Verlag, Germany.

Throughout the description and Examples, reference is made to the following sequences:
   SEQ ID NO: 1: oligonucleotide primer for the amplification of the RG1 PSTVd;
   SEQ ID NO: 2: oligonucleotide primer for the amplification of the RG1 PSTVd;
   SEQ ID NO: 3: nucleotide sequence of the genome of PSTVd RG1;
   SEQ ID NO: 4: nucleotide sequence of genome of the Australian grapevine viroid;
   SEQ ID NO: 5: nucleotide sequence of the genome of the Coconut tinangaja viroid;
   SEQ ID NO: 6: nucleotide sequence of the genome of the Tomato planta macho viroid;
   SEQ ID NO: 7: nucleotide sequence of the genome of the Hop latent viroid;
   SEQ ID NO: 8: nucleotide sequence of the genome of the Tomato apical stunt viroid;
   SEQ ID NO: 9: nucleotide sequence of the pdk2 intron;
   SEQ ID NO: 10: nucleotide sequence of the EIN2 cDNA;
   SEQ ID NO: 11: nucleotide sequence the genomic EIN2 clone;

SEQ ID NO: 12: oligonucleotide primer 1 for the amplification of the EIN2 part used in the constructs in the Examples;

SEQ ID NO: 13: oligonucleotide primer 2 for the amplification of the EIN2 part used in the constructs in the Examples;

SEQ ID NO: 14: pTSVd sequence in pMBW491;

SEQ ID NO: 15: pTSVd sequence in pMBW489 (with 10 nt deletion).

EXAMPLES

Example 1

Construction of the Different Plant Lines Containing Different Chimeric Genes Used As an example target gene to downregulate the expression using the various constructs, the EIN2 gene from *Arabidopsis thaliana* was chosen. The downregulation of the expression of the EIN2 gene can easily be visualized by germinating seeds on MS-ACC medium (containing aminocyclopropane-1-carboxylic acid (ACC)) and incubating either in the dark or in light.

Figure 3:
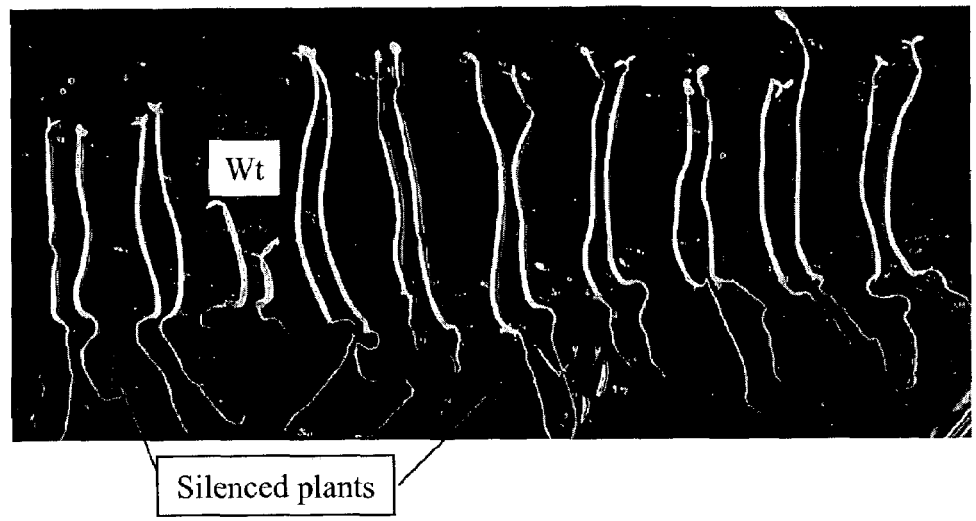
FIG. 3: Phenotype of EIN2-silenced plants when germinating on 1-aminocyclopropane-1-carboxylic acid (ACC). A. In the dark; B. under light conditions. Wt: wild-type plants.
Figure 3:
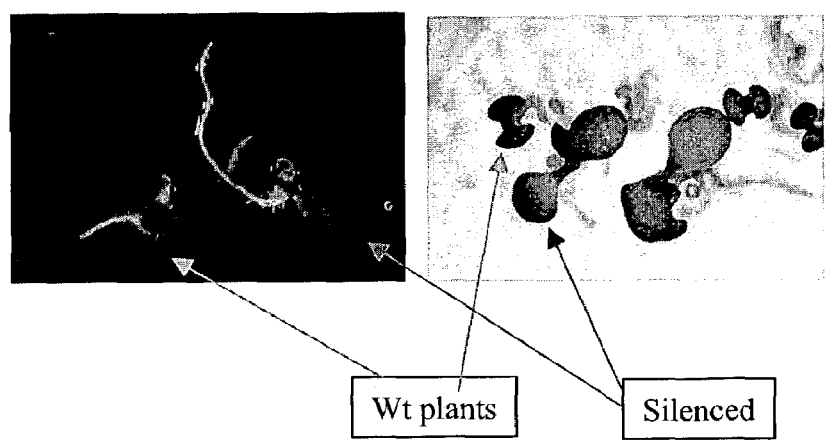
Figure 4:
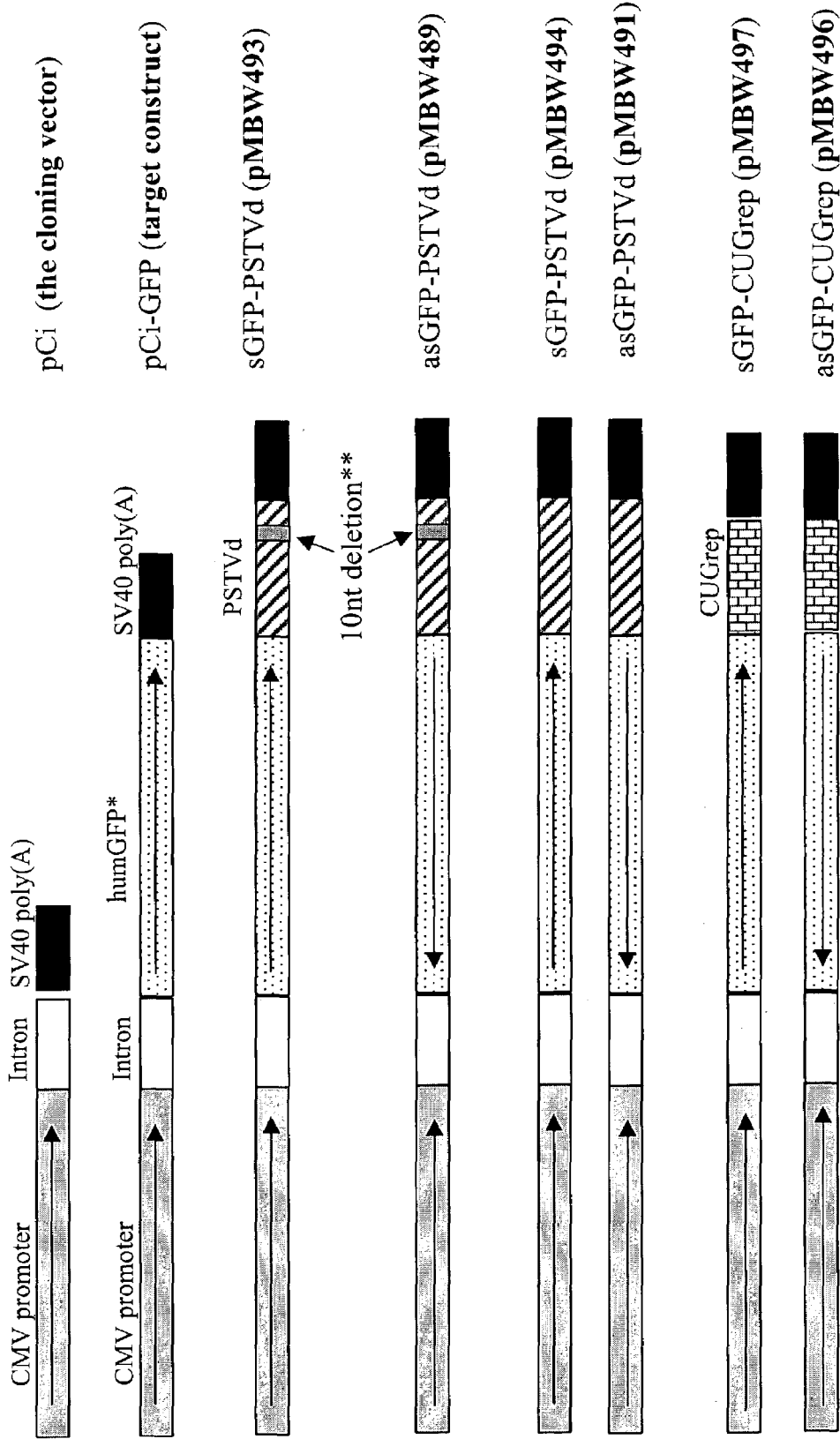
FIG. 4: schematic representation of the various chimeric gene constructs used in Example 4. CMV promoter: cytomegalovirus promoter; SV40 poly(A): transcription termination and polyadenylation region from SV40; PSTVd: potato spindle tuber viroid sequence; CUGrep: sequence comprising 60 repeats of the CUG sequence; humGFP: humanized green fluorescent protein coding region (adapted to the codon usage of human genes; the orientation of this region with respect to the promoter is indicated by the arrow).

Dark-grown EIN2 silenced seedlings grown in the dark have a longer hypocotyl and a more developed root system compared to wildtype ("wt") seedlings, whereas EIN2 silenced seedlings grown in light can be differentiated from the wt seedlings by their larger cotyledon size (see FIG. 3).

The EIN2 nucleotide sequence to be used in the different constructs in sense or antisense orientation was amplified by PCR using oligonucleotide primers with a nucleotide sequence as represented in SEQ ID NO: 12 and 13 using genomic DNA (nucleotide sequence see SEQ ID NO: 11) or cDNA (nucleotide sequence see SEQ ID NO: 10) as template DNA. The amplification of the genomic EIN2 sequence part (gEIN2) resulted in a PCR fragment with the nucleotide sequence of SEQ ID NO: 11 from the nucleotide at position 538 to the nucleotide at position 1123 and contains two native introns of the EIN2 gene.

The gEIN2 fragment was cloned as a KpnII/ClaI fragment into pART7 (Gleave, 1992 Plant. Mol. Biol. 20: 1203-1207), resulting in pMBW313 and the 35S promoter-gEIN2$_{sense}$-OCS3' cassette was cloned into pART27 (Gleave 1992 supra) at the NotI site to result in pMBW353.

A similar fragment (cEIN2) was amplified by PCR using EIN2 cDNA (SEQ ID NO: 10) as template and the same pair of primers as for gEIN2. The cEIN2 fragment was digested with BamHI/ClaI and cloned into pSHUTTLE (Wang et al., 1998 Acta Hort. 461: 401-407) at the same sites, giving pMBW310. The cEIN2 fragment was then excised from pMBW310 with XbaI and cloned into the XbaI site of pART7, forming pMBW351. From this intermediate vector the 35S-EIN2antisense-OCS3' cassette was excised and cloned into pWBVec2A (Wang et al. 1998, supra) at the NotI site, resulting in pMBW360.

A full-length sequence of the PSTVd strain RG1 (SEQ ID NO: 3) was amplified from a cDNA using oligonucleotides with the nucleotide sequence of SEQ ID NO: 1 and SEQ ID NO: 2. The resulting PCR fragment was digested with BglII and cloned into the BamHI site of pMBW313, resulting in pMBW345, from which the 35S-gEIN2-PSTVd-OCS3' cassette was excised and cloned into pART27 at the NotI site resulting in pMBW355.

For pMBW359 the PCR amplified PSTVd sequence was digested with BgII and cloned into the BamHI site of pMBW310, giving pMBW346, from which the cEIN2antisense-PSTVd sequence was excised with XbaI and cloned into the XbaI site of pHANNIBAL (Wesley et al. 2001), forming pMBW349. The 35S-pdk2-cEIN2antisense-PSTVd-OCS3' cassette was then cloned into pWBVec2a at the NotI site forming pMBW359. The cEIN2antisense PSTVd fragment was also cloned into pWBVec2a to yield pMBW357.

The EIN2 cDNA fragment was excised form pMBW310 with EcoRV/BamHI, blunted by Pfu treatment and ligated into the BamHI site (also Pfu treated) of pKANNIBAL (Wesley et al. 2001). Plasmids having the cEIN2 in both orientations with respect to the 35S promoter were recovered and named pMWB401 (antisense) and pMBW404 (sense orientation).

For pLMW37, pLMW38, pLMW39, and pLMW40 the cEIN2 fragment was inserted in sense or antisense orientation upstream or downstream of an inverted repeat of the PSTVd sequence. To this end, a partial PSTVd sequence (SEQ ID NO: 3 from the nucleotide at position 16 to the nucleotide at position 355) was cloned upstream of the pdk intron in inverse orientation with regard to the complete copy of the PSTVd genome.

The different constructs are schematically represented in FIG. 2.

Example 2

Analysis of Expression of the EIN2 Gene in Transgenic *Arabidopsis* Lines Comprising the Different Chimeric Genes of Example 1.

The chimeric constructs represented in FIG. 2 were introduced into *Agrobacterium tumefaciens* using conventional methods and the resulting *Agrobacterium* strains were used to introduce the chimeric genes into *Arabidopsis* ecotype Landsberg erecta through the dipping method. Transgenic lines were selected on 15 mg/L hygromycin or 50 mg/L kanamycin as the selective agent. T1 opr F1 seed was collected and assayed for EIN2 silencing.

To this end, the seed was plated on MS medium containing 50 μM ACC. The plates were sealed tightly with parafilm and kept either under light or in the dark. Silencing was scored by looking at the size of roots and cotyledons (incubation in the light) or by looking at the size of roots or hypocotyls (incubation in the dark). In EIN2 silenced lines, the roots or hypocotyls are significantly longer, and the cotyledons are significantly larger than in wt lines grown under the same conditions.

Seed from primary transformants was plated on MS-ACC medium, sealed with Parafilm, kept at 4° C. for 0-2 overnights, and then moved to growth room and kept either under light or in the dark. Silencing of the EIN2 gene was scored by examining the size of the roots and cotyledons (for those germinating under light) or the size of hypocotyls (for those in the dark). Significant or strong silencing means long roots or hypocotyls, while weak silencing means bigger cotyledons but short roots or hypocotyls. The results are summarized in Table 1.

TABLE 1

Summary of the efficiency of EIN2 silencing in *A. thaliana* plants transformed with various EIN2 constructs.

| Construct | Short description | # transgenic lines | # strong silencing | # weak silencing | Frequency of silencing |
|---|---|---|---|---|---|
| PMBW360 | EIN2 antisense | 23 | 2 | 5 | 30% |
| PMBW401 | EIN2 antisense Pdk intron | 20 | 0 | 3 | 15% |
| PMBW357 | EIN2 antisense PSTVd | 17 | 3 | 5 | 47% |
| PMBW359 | EIN2 antisense PSTVd Pdk intron | 22 | 10 | 6 | 73% |
| PMBW353 | EIN2 sense Native introns | 19 | 2 | 3 | 26% |
| PMBW355 | EIN2 sense Native introns PSTVd | 17 | 1 | 1 | 12% |
| PMBW404 | EIN 2 sense PDK intron | 20 | 3 | 2 | 25% |
| PLMW37 | EIN2 sense Pdk intron PSTVd repeat | 19 | 0 | 0 | 0 |
| PLMW38 | EIN2 antisense Pdk intron PSTVd repeat | 10 | 1 | 2 | 30 |
| PLMW39 | EIN2 sense Pdk intron PSTVd repeat | 17 | 0 | 0 | 0 |
| PLMW40 | EIN2 antisense Pdk intron PSTVd repeat | 20 | 2 | 5 | 35% |

Example 3

Analysis of Expression of the EIN2 Gene in *Arabidopsis* Lines Obtained by Crossing of the Transgenic *Arabidopsis* Lines Comprising the Different Chimeric Genes of Example 1.

By cross-pollination between the *Arabidopsis* lines MBW353, MBW355, MBW359, and MBW360 new lines were obtained simultaneously containing sense and antisense EIN2 constructs. These new lines were analyzed in a similar way as described in Example 2. The results are summarized in Table 2. Plants wherein at least one of the transgenes contained a PSTVd sequence were very efficiently silenced.

TABLE 2

Summary of the efficiency of EIN2 silencing in *A. thaliana* plants comprising different combination of sense and antisense EIN2 constructs.

| Line | Short description | N° of lines tested | N° of lines silenced | Frequency of silencing |
|---|---|---|---|---|
| MBW353 X MB360 | EIN2 sense Native introns And EIN2 antisense | 7 | 2 | 28.5% |
| MBW353 X MBW359 | EIN2 sense Native introns And EIN2 antisense PSTVd Pdk intron | 3 | 3 | 100% |
| MBW355 X | EIN2 sense Native introns | 5 | 4 | 80% |
| MBW360 | PSTVd And EIN2 antisense | | | |
| MBW355 X MBW359 | EIN2 sense Native introns PSTVd And EIN2 antisense PSTVd Pdk intron | 11 | 9 | 81.8% |

Example 4

Construction of Different Chimeric Genes for Mediating Gene Silencing of a GFP Gene in Mammalian Cells and Analysis in CHO Cells.

As an example target gene to down-regulate the expression in mammalian cells, the humanized GFP coding region, expressed under control of a CMV promoter region, and followed by a SV40 polyadenylation signal was chosen (pCI-GFP).

Different experimental silencing constructs were constructed, having either the GFP coding region cloned in sense (as in pMBW493, pMBW494 and pMBW497) or antisense orientation (as in pMBW489, pMBW491 or pMBW496) with regard to the CMV promoter region.

Figure 5:
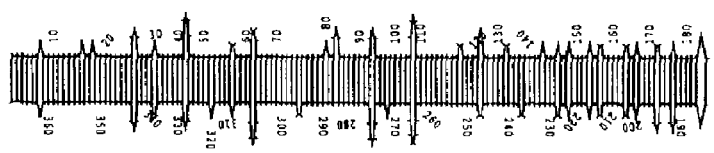
FIG. 5: Schematic representation of the predicted secondary structure of pSTVd in pMBW491 (A; adopting almost the wild-type configuration) and in pMBW489, where a 10 nucleotide deletion results in a structure different from the wild-type configuration.
Figure 5:
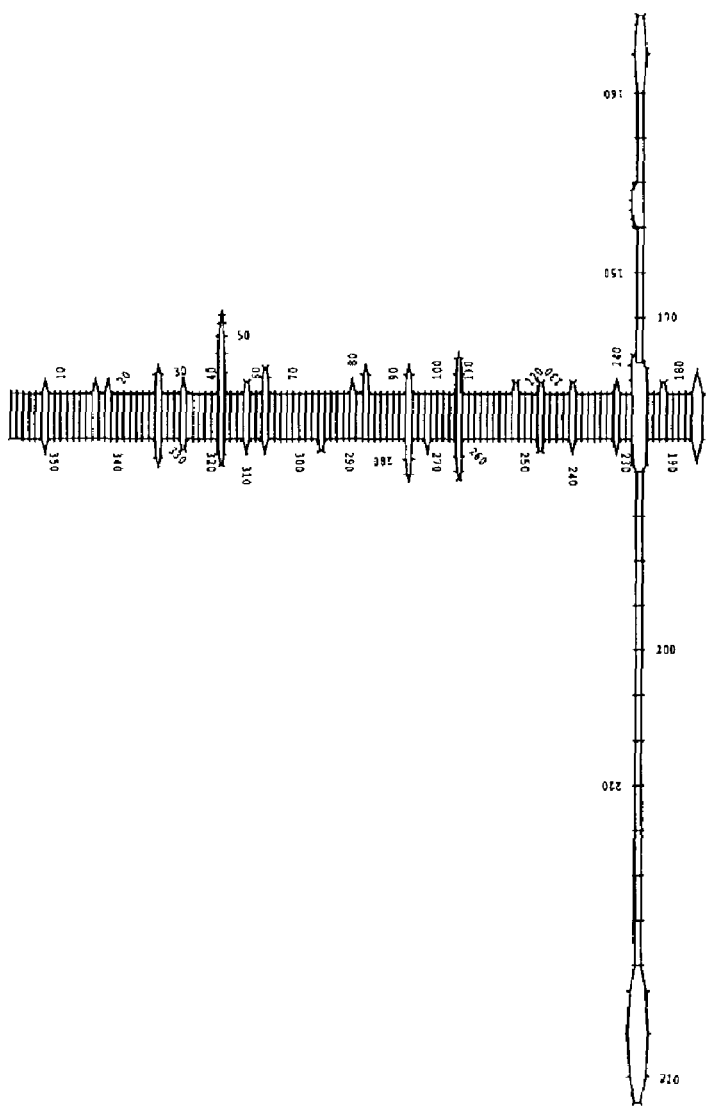

Plasmids pMBW493 and pMBW489 contained downstream of the GFP coding region, but upstream of the SV40 polyadenylation signal, a nucleotide sequence corresponding to a PSTVd sequence but with a 10 nt deletion (SEQ ID NO: 15). This deletion impacts the predicted secondary structure (see FIG. 5).

Plasmids pMBW494 and pMBW491 contained downstream of the GFP coding region, but upstream of the SV40 polyadenylation signal, a nucleotide sequence corresponding to a PSTVd sequence of SEQ ID NO: 14 without the 10 nt deletion.

Plasmids pMBW497 and pMBW496 contained downstream of the GFP coding region, but upstream of the SV40 polyadenylation signal, a nucleotide sequence comprising 60 CUG trinucleotide repeats.

The different experimental plasmids were introduced (at different concentrations) into CHO cells in combination with a plasmid comprising the GFP expressing chimeric gene (Table 3; entries 1 to 18). Since the GFP construct is a functional sequence in the sense constructs, sense GFP containing experimental constructs were also introduced without the extra GFP expressing chimeric gene; to estimate the GFP expression by these constructs alone (Table 3; entries 19 to 30). Further, combinations of antisense and sense experimental constructs were introduced in CHO cells, at different concentrations (Table 3; entries 31 to 42). As a control, the chimeric GFP expression construct (pCi-GFP) was introduced alone into CHO cells.

After 24 hrs or 48 hrs, the cells were assayed for GFP expression. Average counts and standard deviations are represented in Table 3.

Table 3. Summary of GFP expression in into CHO cells transformed by the different experimental constructs.

| | Experimental DNA | Target DNA | Remarks on Experimental DNA | Average count (24 hr) | Standard deviation | Average count (48 hr) | Standard deviation |
|---|---|---|---|---|---|---|---|
| 1 | 0.1 μg pMBW89 | 0.3 μg GFP | Antisense + PSTVd (deletion) | 3626 | 206 | 9058 | 1468 |
| 2 | 0.3 μg pMBW89 | 0.3 μg GFP | | 3521 | 41 | 6468 | 3522 |
| 3 | 0.7 μg pMBW89 | 0.3 μg GFP | | 3167 | 1348 | 1096 | 2191 |
| 4 | 0.1 μg MBW91 | 0.3 μg GFP | Antisense + PSTVd | 3585 | 86 | 5908 | 623 |
| 5 | 0.3 μg pMBW91 | 0.3 μg GFP | | 748 | 128 | 1426 | 332.3 |
| 6 | 0.7 μg pMBW91 | 0.3 μg GFP | | 23 | 25 | 1637 | 70 |
| 7 | 0.1 μg pMBW96 | 0.3 μg GFP | Antisense + CUG repeats | 3217 | 467 | 5221 | 4700 |
| 8 | 0.3 μg pMBW96 | 0.3 μg GFP | | 2907 | 107 | 3272 | 0 |
| 9 | 0.7 μg pMBW96 | 0.3 μg GFP | | 181 | 92 | 1433 | 466 |
| 10 | 0.1 μg pMBW93 | 0.3 μg GFP | Sense + PSTVd (deletion) | 5815 | 313 | 16482 | 470 |
| 11 | 0.3 μg pMBW93 | 0.3 μg GFP | | 10453 | 1555 | 15810 | 1067 |
| 12 | 0.7 μg pMBW93 | 0.3 μg GFP | | 12718 | 5423 | 10666 | 949 |
| 13 | 0.1 μg pMBW94 | 0.3 μg GFP | Sense + PSTVd | 9166 | 1269 | 15023 | 263 |
| 14 | 0.3 μg MBW94 | 0.3 μg GFP | | 12719 | 3894 | 6699 | 94 |
| 15 | 0.7 μg MBW94 | 0.3 μg GFP | | 1009 | 658 | 13133 | 824 |
| 16 | 0.1 μg MBW97 | 0.3 μg GFP | Sense + CUG repeats | 6414 | 1367 | 15795 | 178 |
| 17 | 0.3 μg pMBW97 | 0.3 μg GFP | | 3596 | 50 | 10235 | 770 |
| 18 | 0.7 μg pMBW97 | 0.3 μg GFP | | 729 | 295 | 13171 | 2868 |
| 19 | 0.1 μg pMBW93 | None | Sense + PSTVd (deletion) | 1216 | 15 | 3692 | 142 |
| 20 | 0.3 μg pMBW93 | None | | 6022 | 1293 | 9341 | 273 |
| 21 | 0.5 μg pMBW93 | None | | 6795 | 3235 | 11466 | 2541 |
| 22 | 0.7 μg pMBW93 | None | | 12002 | 763 | 10316 | 1523 |
| 23 | 0.1 μg pMBW94 | None | Sense + PSTVd | 2121 | 594 | 5417 | 777 |
| 24 | 0.3 μg MBW94 | None | | 5671 | 5096 | 9317 | 743 |
| 25 | 0.5 μg pMBW94 | None | | 6349 | 3253 | 7842 | 337 |
| 26 | 0.7 μg MBW94 | None | | 1785 | 729 | 15574 | 2208 |
| 27 | 0.1 μg MBW97 | None | Sense + CUG repeats | 4448 | 626 | 6064 | 289 |
| 28 | 0.3 μg MBW97 | None | | 487 | 83 | 7767 | 194 |
| 29 | 0.5 μg pMBW97 | None | | 522 | 223 | 7481 | 566 |
| 30 | 0.7 μg pMBW97 | None | | 270 | 159 | 8980 | 1154 |
| 31 | 0.1 μg pMBW 93 + 0.1 μg pMBW 91 | None | Sense + PSTVd (deletion) and Antisense + PSTVd | 1189 | 148 | 2331 | 815 |
| 32 | 0.3 μg pMBW 93 + 0.3 μg pMBW 91 | None | | 695 | 83 | 3101 | 533 |
| 33 | 0.5 μg pMBW 93 + 0.5 μg pMBW 91 | None | | 111 | 117 | 3758 | 1583 |

-continued

| Experimental DNA | Target DNA | Remarks on Experimental DNA | Average count (24 hr) | Standard deviation | Average count (48 hr) | Standard deviation |
|---|---|---|---|---|---|---|
| 34 0.3 µg pMBW 93 +0.1 µg pMBW 91 | None | | 1811 | 1304 | 5301 | 73 |
| 35 0.3 µg pMBW 93 + 0.3 µg pMBW 91 | None | | 312 | 171 | 4972 | 401 |
| 36 0.3 µg pMBW 93 +0.1 µg pMBW 91 | None | | 14 | 20 | 2896 | 1075 |
| 37 0.1 µg pMBW 97 + 0.1 µg pMBW 96 | None | Antisense + CUG repeats and | 3841 | 929 | 2945 | 341 |
| 38 0.3 µg pMBW 97 + 0.3 µg pMBW 96 | None | Sense + CUG repeats | 1018 | 401 | 3236 | 822 |
| 39 0.5 µg pMBW 97 + 0.5 µg pMBW 96 | None | | 1262 | 241 | 6730 | 289 |
| 40 0.3 µg pMBW 97 + 0.1 µg pMBW 96 | None | | 3603 | 2785 | 10349 | 3463 |
| 41 0.3 µg pMBW 97 + 0.3 µg pMBW 96 | None | | 4903 | 1054 | 3453 | 2380 |
| 42 0.3 µg pMBW 97 +0.7 µg pMBW 96 | none | | 278 | 46 | 5897 | 1899 |
| 43 None | 0.3 µg GFP | Control | 4780 | 688 | 25175 | 8289.6 |

The antisense GFP constructs pMBW491, pMBW496 and pMBW489 that carry the pTSVd or CUG repeat sequences resulted in a significant reduction of the expression of the GFP gene.

Interestingly, pMWB489 in which the PSTVd sequence contains a 10 nt deletion, resulted in slower and lower degrees of GFP silencing than pMWB491, which contains an intact PSTVd sequence.

We claim:

1. A method for downregulating the expression of a target gene in cells of a plant, comprising the steps of:
   providing the cells of the plant with a chimeric RNA molecule, wherein the chimeric RNA molecule comprises
   a target gene-specific RNA region comprising a nucleotide sequence of at least about 50 consecutive nucleotides, which has at least about 94% sequence identity with the complement of about 50 consecutive nucleotides from the nucleotide sequence of the target gene, operably linked to
   a largely double-stranded RNA region that folds into a rod-like structure by internal base-pairing, said rod-like structure comprising non-matching nucleotides which bulge out from within said structure, and wherein said RNA molecule does not comprise any double stranded RNA region of at least 19 consecutive matching basepairs or any double stranded region of 19 consecutive basepairs having only one mismatch, wherein the largely double-stranded RNA region localizes the chimeric RNA to the nucleus of said cells; and
   wherein said cells have an increased concentration of said chimeric RNA molecule in the nucleus relative to cytoplasm of said cells compared to cells of a plant provided with an RNA molecule having said target gene specific RNA region but lacking said largely double stranded RNA region, and wherein the expression of the target gene is downregulated,
   wherein the largely double-stranded RNA region comprises the viroid genome nucleotide sequence selected from the group consisting of the genome nucleotide sequence of Potato Spindle tuber viroid, the genome nucleotide sequence of Citrus viroid species III, the genome nucleotide sequence of Citrus viroid species IV, the genome nucleotide sequence of Hop latent viroid, the genome nucleotide sequence of Australian grapevine viroid, the genome nucleotide sequence of Tomato planta macho viroid, the genome nucleotide sequence of Coconut tinangaja viroid, the genome nucleotide sequence of Tomato apical stunt viroid, the genome nucleotide sequence of Coconut cadang-cadang viroid, the genome nucleotide sequence of *Citrus exocortis* viroid, the genome nucleotide sequence of Columnea latent viroid, the genome nucleotide sequence of Hop stunt viroid and the genome nucleotide sequence of Citrus bent leaf viroid.

2. The method according to claim 1, wherein the largely double-stranded RNA region comprises the nucleotide sequence of SEQ ID NO: 3.

3. The method according to claim 1, wherein the viroid genome nucleotide sequence is selected from the group consisting of SEQ ID NO: 3, SEQ ID NO: 4, SEQ ID NO: 5, SEQ ID NO:6, SEQ ID NO:7 and SEQ ID NO:8.

4. The method according to claim 1, wherein the viroid genome nucleotide sequence is the genome nucleotide sequence of Potato spindle tuber viroid strain RG1.

5. The method of claim 4, wherein the genome nucleotide sequence has the nucleotide sequence of SEQ ID NO:3.

6. The method according to claim 1, wherein the RNA molecule comprises multiple target gene-specific regions.

7. The method according to claim 1, wherein the plant is selected from the group of *Arabidopsis*, alfalfa, barley, bean, corn, cotton, flax, pea, rape, rice, rye, safflower, sorghum, soybean, sunflower, tobacco, wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

8. The method according to claim 1, wherein the chimeric RNA is produced by transcription from a chimeric DNA molecule.

9. A chimeric RNA molecule for downregulating the expression of a target gene in a cell of a plant, comprising
a target-gene specific RNA region comprising a nucleotide sequence of at least about 50 consecutive nucleotides, which has at least about 94% sequence identity with the complement of about 50 consecutive nucleotides from the nucleotide sequence of the target gene in the cells of the plant; operably linked to
a largely double stranded RNA region that folds into a rod-like structure by internal base-pairing, said rod-like structure comprising non-matching nucleotides which bulge out from within said structure, and wherein said RNA molecule does not comprise any double stranded RNA region of at least 19 consecutive matching basepairs or any double stranded region of 19 consecutive basepairs having only one mismatch, wherein the largely double-stranded RNA region localizes the chimeric RNA to the nucleus of said cells;
wherein the chimeric RNA molecule, when provided to cells of the plant, has an increased concentration in the nucleus relative to cytoplasm of said cells compared to cells of a plant provided with an RNA molecule having said target gene specific RNA region but lacking said largely double stranded RNA region and wherein said chimeric RNA molecule, when provided to cells of the plant, downregulates the expression of the target gene, and wherein the largely double-stranded RNA region comprises the viroid genome nucleotide sequence selected from the group consisting of the genome nucleotide sequence of Potato Spindle tuber viroid, the genome nucleotide sequence of Citrus viroid species III, the genome nucleotide sequence of Citrus viroid species IV, the genome nucleotide sequence of Hop latent viroid, the genome nucleotide sequence of Australian grapevine viroid, the genome nucleotide sequence of Tomato planta macho viroid, the genome nucleotide sequence of Coconut tinangaja viroid, the genome nucleotide sequence of Tomato apical stunt viroid, the genome nucleotide sequence of Coconut cadang-cadang viroid, the genome nucleotide sequence of *Citrus exocortis* viroid, the genome nucleotide sequence of Columnea latent viroid, the genome nucleotide sequence of Hop stunt viroid and the genome nucleotide sequence of Citrus bent leaf viroid.

10. The chimeric RNA molecule according to claim 9, wherein the largely double stranded RNA region comprises the nucleotide sequence of SEQ ID NO: 3.

11. The chimeric RNA molecule according to claim 9, wherein the viroid genome nucleotide sequence is selected from group consisting of SEQ ID NO:3, SEQ ID NO:4, SEQ ID NO:5, SEQ ID NO:6, SEQ ID NO:7 and SEQ ID NO:8.

12. The chimeric RNA molecule according to claim 9, wherein the viroid genome nucleotide sequence is the genome nucleotide sequence of Potato spindle tuber viroid strain RG1.

13. The chimeric RNA molecule of claim 12, wherein the genome nucleotide sequence has the nucleotide sequence of SEQ ID NO:3.

14. The chimeric RNA molecule according to claim 9, wherein the RNA molecule comprises multiple target gene-specific regions.

15. A chimeric DNA molecule for reduction of the expression of a target gene in a cell of a plant, comprising a promoter or promoter region capable of being recognized by RNA polymerases in the cells of the plant, operably linked to a DNA region that, when transcribed, yields a chimeric RNA molecule comprising a target gene-specific RNA region comprising a nucleotide sequence of at least about 50 consecutive nucleotides having at least about 94% sequence identity with the complement of 50 consecutive nucleotides from the nucleotide sequence of the target gene in the cells of the plant, operably linked to a largely double-stranded RNA region that folds into a rod-like structure by internal base-pairing, said rod-like structure comprising non-matching nucleotides which bulge out from within said structure, and wherein said RNA molecule does not comprise any double stranded RNA region of at least 19 consecutive matching basepairs or any double stranded region of 19 consecutive basepairs having only one mismatch, wherein the largely double-stranded RNA region localizes the chimeric RNA to the nucleus of said cells;

wherein the chimeric DNA molecule, when provided to cells of the plant, yields an increased concentration of the chimeric RNA molecule in the nucleus relative to cytoplasm of said cell compared to cells of a plant provided with an RNA molecule having said target gene specific RNA region but lacking said largely double stranded RNA region and wherein said chimeric RNA molecule, when provided to cells of the plant, reduces the expression of the target gene, and wherein the largely double-stranded RNA region comprises the viroid genome nucleotide sequence selected from the group consisting of the genome nucleotide sequence of Potato Spindle tuber viroid, the genome nucleotide sequence of Citrus viroid species III, the genome nucleotide sequence of Citrus viroid species IV, the genome nucleotide sequence of Hop latent viroid, the genome nucleotide sequence of Australian grapevine viroid, the genome nucleotide sequence of Tomato planta macho viroid, the genome nucleotide sequence of Coconut tinangaja viroid, the genome nucleotide sequence of Tomato apical stunt viroid, the genome nucleotide sequence of Coconut cadang-cadang viroid, the genome nucleotide sequence of *Citrus exocortis* viroid, the genome nucleotide sequence of Columnea latent viroid, the genome nucleotide sequence of Hop stunt viroid and the genome nucleotide sequence of Citrus bent leaf viroid.

16. The chimeric DNA molecule according to claim 15, wherein the largely double stranded RNA region comprises the nucleotide sequence of SEQ ID NO: 3.

17. The chimeric DNA molecule according to claim 15, wherein the viroid genome nucleotide sequence is selected from group consisting of SEQ ID NO: 3, SEQ ID NO:4, SEQ ID NO: 5, SEQ ID NO: 6, SEQ ID NO: 7 and SEQ ID NO: 8.

18. The chimeric DNA molecule according to claim 15, wherein the viroid genome nucleotide sequence is the genome nucleotide sequence of Potato spindle tuber viroid strain RG1.

19. The chimeric DNA molecule of claim 18, wherein the genome nucleotide sequence has the nucleotide sequence of SEQ ID NO: 3.

20. The chimeric DNA molecule according to claim 15, wherein the RNA molecule comprises multiple target gene-specific regions.

21. The chimeric DNA molecule according to claim 15, further comprising a transcription termination and polyadenylation signal operably linked to the DNA region encoding the RNA molecule.

22. The chimeric DNA molecule according to claim 15, wherein the promoter or promoter region is recognized by a single subunit bacteriophage RNA polymerase.

23. A cell from a plant comprising a chimeric DNA molecule according to claim 15.

24. A plant cell comprising a chimeric RNA molecule according to claim 9.

25. The cell according to 23, wherein the plant is selected from the group of *Arabidopsis*, alfalfa, barley, bean, corn, cotton, flax, pea, rape, rice, rye, safflower, sorghum, soybean, sunflower, tobacco, wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

26. A plant comprising in its cells a chimeric DNA molecule according to claim 15.

27. A plant, comprising in its cells a chimeric RNA molecule according to claim 9.

28. The plant according to 26, wherein the plant is selected from the group of *Arabidopsis*, alfalfa, barley, bean, corn, cotton, flax, pea, rape, rice, rye, safflower, sorghum, soybean, sunflower, tobacco, wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

29. A method for making a transgenic plant in which expression of a target gene in cells of the plant is reduced, the method comprising the steps of:
providing a chimeric DNA molecule according to claim 15 to cells of the plant to make transgenic cells; and
growing or regenerating a transgenic plant from the transgenic cells.

30. The method according to claim 1, wherein said rod-like structure is the structure of the largely double stranded RNA region in its energetically most favorable conformation.

31. The method according to claim 1, wherein said rod-like structure comprises stretches of double stranded RNA and wherein the longest stretch of perfectly basepaired RNA is 11 contiguous basepairs in size.

32. The chimeric RNA molecule according to claim 9, wherein said rod-like structure is the structure of the largely double stranded RNA region in its energetically most favorable conformation.

33. The chimeric RNA molecule according to claim 9, wherein said rod-like structure comprises stretches of double stranded RNA and wherein the longest stretch of perfectly basepaired RNA is 11 contiguous basepairs in size.

34. A cell from a plant comprising the chimeric RNA molecule of claim 32.

35. A cell from a plant comprising the chimeric RNA molecule of claim 33.

* * * * *

UNITED STATES PATENT AND TRADEMARK OFFICE
CERTIFICATE OF CORRECTION

PATENT NO. : 7,576,262 B2
APPLICATION NO. : 10/385521
DATED : August 18, 2009
INVENTOR(S) : Wang et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 860 days Delete the phrase "by 860 days" and insert -- by 1,094 days --

Signed and Sealed this

Twenty-seventh Day of April, 2010

David J. Kappos
*Director of the United States Patent and Trademark Office*